US008030282B2

(12) United States Patent
Licari et al.

(10) Patent No.: US 8,030,282 B2
(45) Date of Patent: *Oct. 4, 2011

(54) MOTILIDE POLYMORPHS

(76) Inventors: Peter J. Licari, Fremont, CA (US); Jorge L. Galazzo, Sunnyvale, CA (US); Greg O. Buchanan, Hayward, CA (US); Alexander Redvers Eberlin, Cambridge (GB); Mark D. Eddleston, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/762,190

(22) Filed: Apr. 16, 2010

(65) Prior Publication Data
US 2010/0227829 A1 Sep. 9, 2010

Related U.S. Application Data

(63) Continuation of application No. 11/987,810, filed on Dec. 4, 2007, now Pat. No. 7,872,109.

(60) Provisional application No. 60/873,101, filed on Dec. 5, 2006.

(51) Int. Cl.
A61K 31/70 (2006.01)
C07H 17/08 (2006.01)
(52) U.S. Cl. .......................... 514/29; 536/7.4
(58) Field of Classification Search .................. None
See application file for complete search history.

(56) References Cited

U.S. PATENT DOCUMENTS

| | | | |
|---|---|---|---|
| 3,855,200 A | 12/1974 | Krowicki et al. |
| 3,939,144 A | 2/1976 | Radobolja et al. |
| 3,983,103 A | 9/1976 | Kobrehel et al. |
| 4,588,712 A | 5/1986 | Toscano et al. |
| 5,008,249 A | 4/1991 | Omura et al. |
| 5,175,150 A | 12/1992 | Omura et al. |
| 5,444,051 A | 8/1995 | Agouridas et al. |
| 5,470,961 A | 11/1995 | Harada et al. |
| 5,523,401 A | 6/1996 | Freiberg et al. |
| 5,523,418 A | 6/1996 | Freiberg et al. |
| 5,538,961 A | 7/1996 | Freiberg et al. |
| 5,554,605 A | 9/1996 | Freiberg et al. |
| 5,561,118 A | 10/1996 | Agouridas et al. |
| 5,578,579 A | 11/1996 | Lartey et al. |
| 5,654,411 A | 8/1997 | Lartey et al. |
| 5,658,888 A | 8/1997 | Koga et al. |
| 5,712,253 A | 1/1998 | Lartey et al. |
| 5,770,579 A | 6/1998 | Agouridas et al. |
| 5,834,438 A | 11/1998 | Lartey et al. |
| 5,922,849 A | 7/1999 | Premchandran et al. |
| 5,959,088 A | 9/1999 | Miura et al. |
| 6,084,079 A | 7/2000 | Keyes et al. |
| 6,169,168 B1 | 1/2001 | Asaka et al. |
| 2002/0025936 A1 | 2/2002 | Ashley et al. |
| 2002/0094962 A1 | 7/2002 | Ashley et al. |
| 2002/0192709 A1 | 12/2002 | Carreras et al. |
| 2004/0138150 A1 | 7/2004 | Santi et al. |
| 2005/0113319 A1 | 5/2005 | Carreras et al. |
| 2005/0119195 A1 | 6/2005 | Carreras et al. |
| 2005/0256064 A1 | 11/2005 | Liu et al. |
| 2006/0270616 A1 | 11/2006 | Liu et al. |
| 2007/0135362 A1 | 6/2007 | Liu |

FOREIGN PATENT DOCUMENTS

| | | |
|---|---|---|
| DE | 2 402 200 A1 | 7/1974 |
| GB | 1 416 281 A | 12/1975 |
| GB | 1 461 032 A | 1/1977 |
| JP | 60-218321 A | 11/1985 |
| JP | 2002-241391 A | 8/2002 |

OTHER PUBLICATIONS

Satoshi Omura et al., "Gastrointestinal Motorstimulating Activity of Macrolide Antibiotics and the Structure-activity Relationship," J. Antibiotics 1985, 38, 1631-32.
Ramin Faghih et al., "Preparation of 9-deoxo-4-deoxy-6,9-epoxyerythromycin Lactams "Motilactides": Potent and Orally Active Prokinetic Agents," Biorg. & Med. Chem. Lett., 1998, 8, 805-810.
Ramin Faghih et al., "Synthesis of 9-Deoxo-4-deoxy-6,9-epoxyerythromycin Derivatives: Novel and Acid-Stable Motilides," J. Med. Chem., 1998, 41, 3402-3408.
Ramin Faghih et al., "Entry into Erythromycin Lactams: Synthesis of Erythromycin A Lactam Enol Ether as a Potential Gastrointestinal Prokinetic Agent," Synlett., Jul. 1998, 751-53. Paul A. Lartey et al., "Synthesis of 4-Deoxy Motilides: Identification of a Potent and Orally Active Prokinetic Drug Candidate," J. Med. Chem., 1995,38,1793-98.
R. Ryden et al., "N-Substituted Derivatives of Erythromycylamine," J. Med. Chem., 1973, 16(9), 1059-60.
Slawomir Naperty et al., "Erythromycin Derivatives. Part IX. Cyclic 8,9-Carbonate of 8-Hydroxyerythromycin B," Roczniki Chemii, 1977, 51(6), 1207-10.

(Continued)

Primary Examiner — Elli Peselev
(74) Attorney, Agent, or Firm — Fitzpatrick, Cella, Harper & Scinto

(57) ABSTRACT

The invention provides polymorphs of a motilide having a structure represented by formula Ia

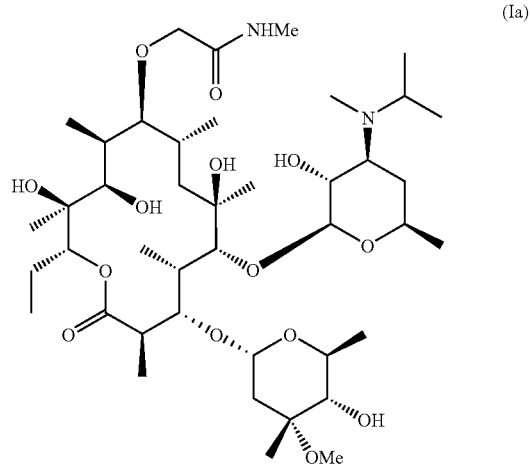

10 Claims, 25 Drawing Sheets

OTHER PUBLICATIONS

Richard S. Egan et al., "The Structures of the m-Chloroperbenzoic Acid Oxidation Products of 8,9-Anhydroerythromycins A- and B-6,9-Hemiacetal and of (8s)-8-Hydroxyerythromycin B," J. Antibiotics, 1978, 31(1), 55-62.

P. Matijasevic et al., "Erythromycin Series. X. Inhibitory Activity of Several New Erythromycin Derivatives in Cell-Free Amino Acid Polymerization Systems," Croatica Chemica Acta, 1980, 53(3), 519-24.

Gorjana Radobolja et al., "Erythromycin Series. IX. Acid Solvolysis of N-(4-Substituted-Benzenesulfonyl) Erythromycylamines," Croatica Chemica Acta, 1985, 58(2), 219-25.

Eric Hunt et al., "9,11-Cyclic Acetal Derivatives of (9s)-9-Dihydroelythromycin A," J. Antibiotics, 1989, 42(2), 293-98.

David C. Myles et al., "Development of a Fully Synthetic Stereoselective Route to 6-Deoxyerythronolide B by Reiterative Applications of the Lewis Acid Catalyzed Diene Aldehyde Cyclocondensation Reaction: A Remarkable Instance of Diastereofacial Selectivity," J. Org. Chem., 1990, 55, 1636-48.

Gabrijela Kobrehel et al., "Erythromycin Series. VIII Synthesis and Biological Activity of N-(Substituted-benzenesulfonyl) Erythromycylamines," Eur. J. Med. Chemistry, 1978, 13(1), 83-87.

N. K. Jain et al., "Polymorphism in Pharmacy," 23(6) Indian Drugs 315-329 (Mar. 1986).

Mino R. Caira, "Crystalline Polymorphism of Organic Compounds," 198 Topics in Current Chemistry 163-208 (1998).

S. R. Byrn et al., "Solid-state Pharmaceutical Chemistry," 6 Chem. Mater. 1148-1158 (1994).

David J. W. Grant, Polymorphism in Pharmaceutical Solids, Chapter 1: Theory and Origin of Polymorphism, pp. 1-10 (1999).

J. Keith Guillory, Polymorphism in Pharmaceutical Solids, Chapter 5: Generation of Polymorphs, Hydrates, Solvates, and Amorphous Solids, pp. 183-226 (1999).

Notification of Defects in Israeli Patent Application No. 198449 (May 30, 2011).

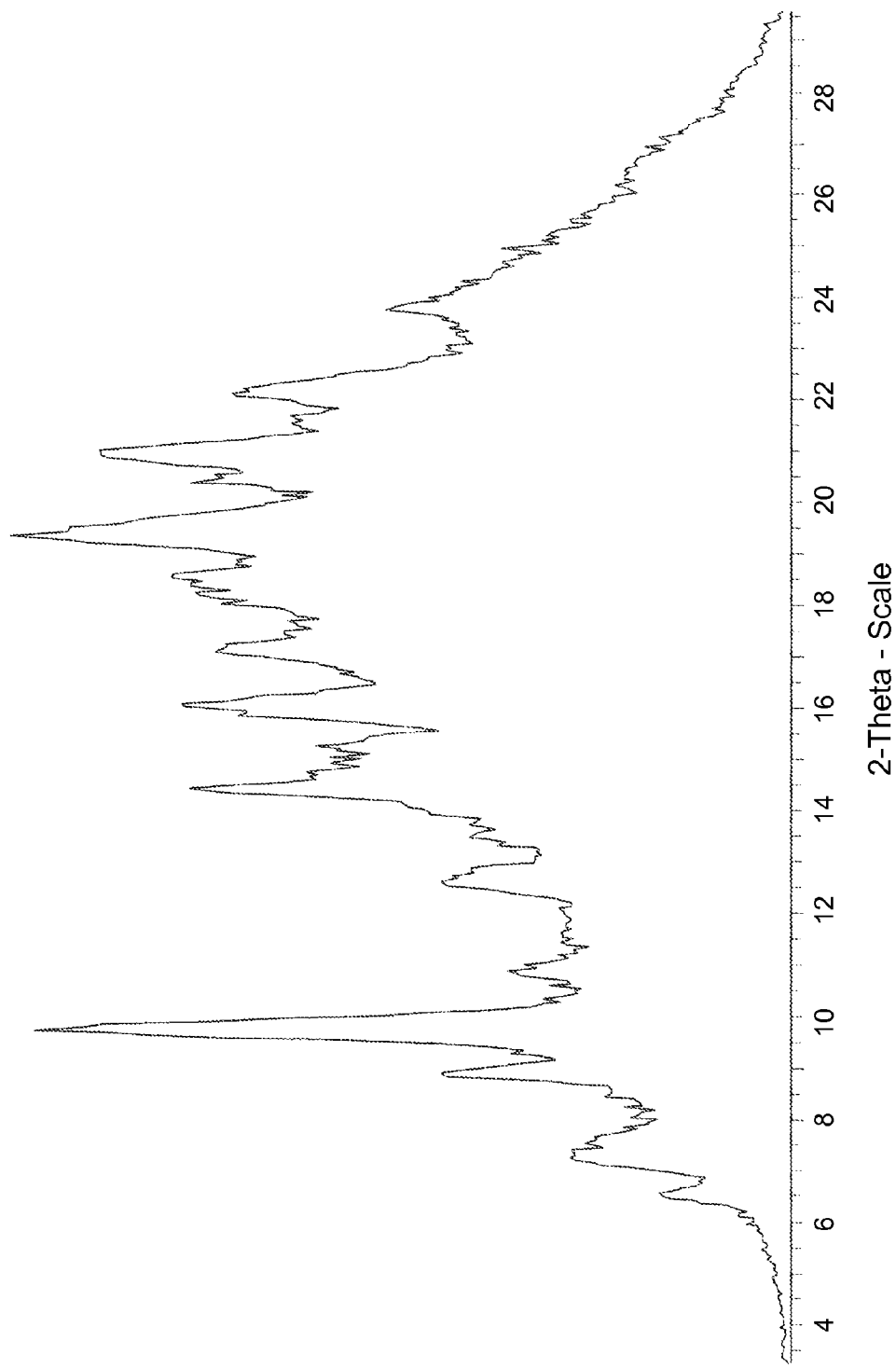

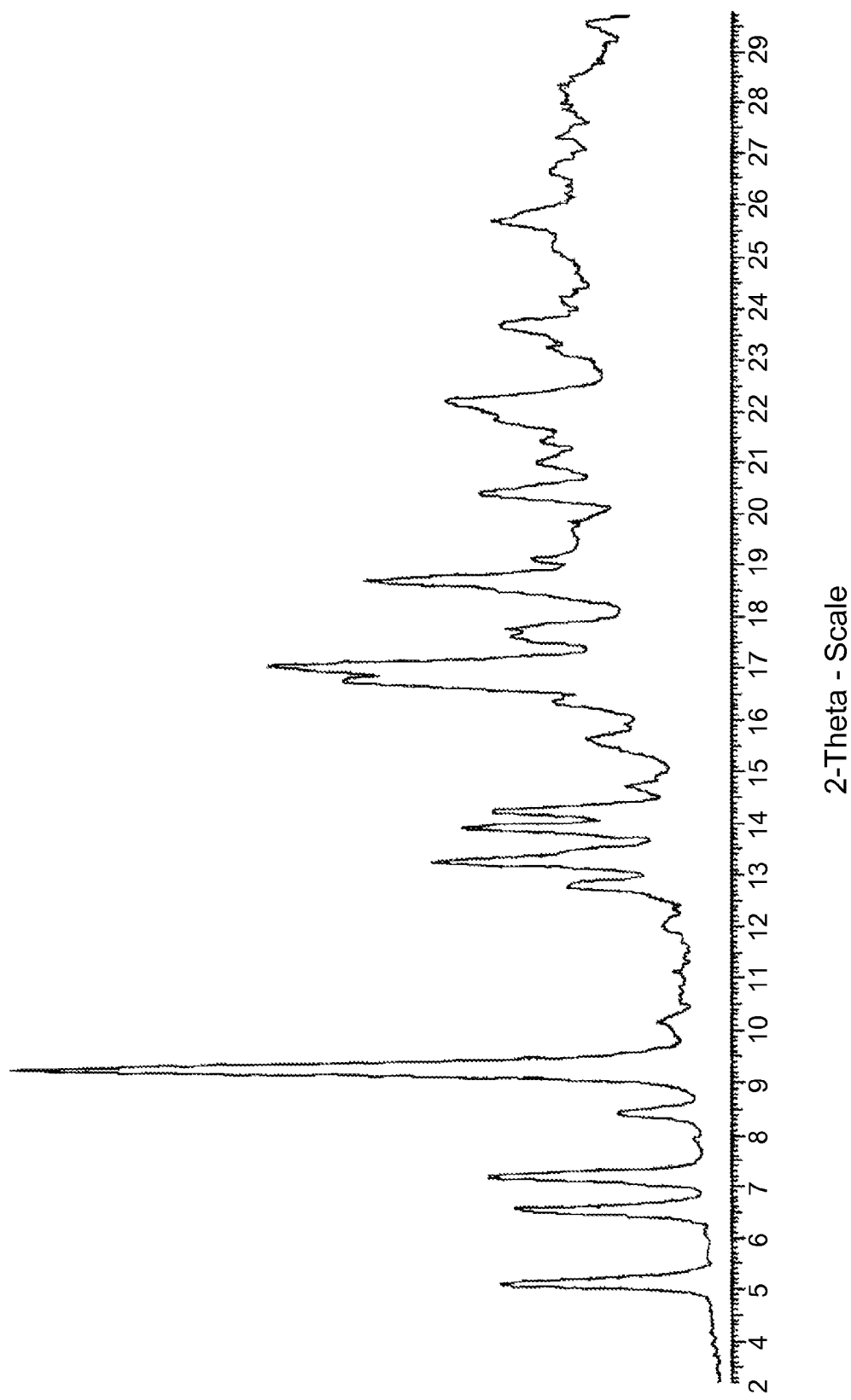
Fig. 1c  XRPD of Polymorph III

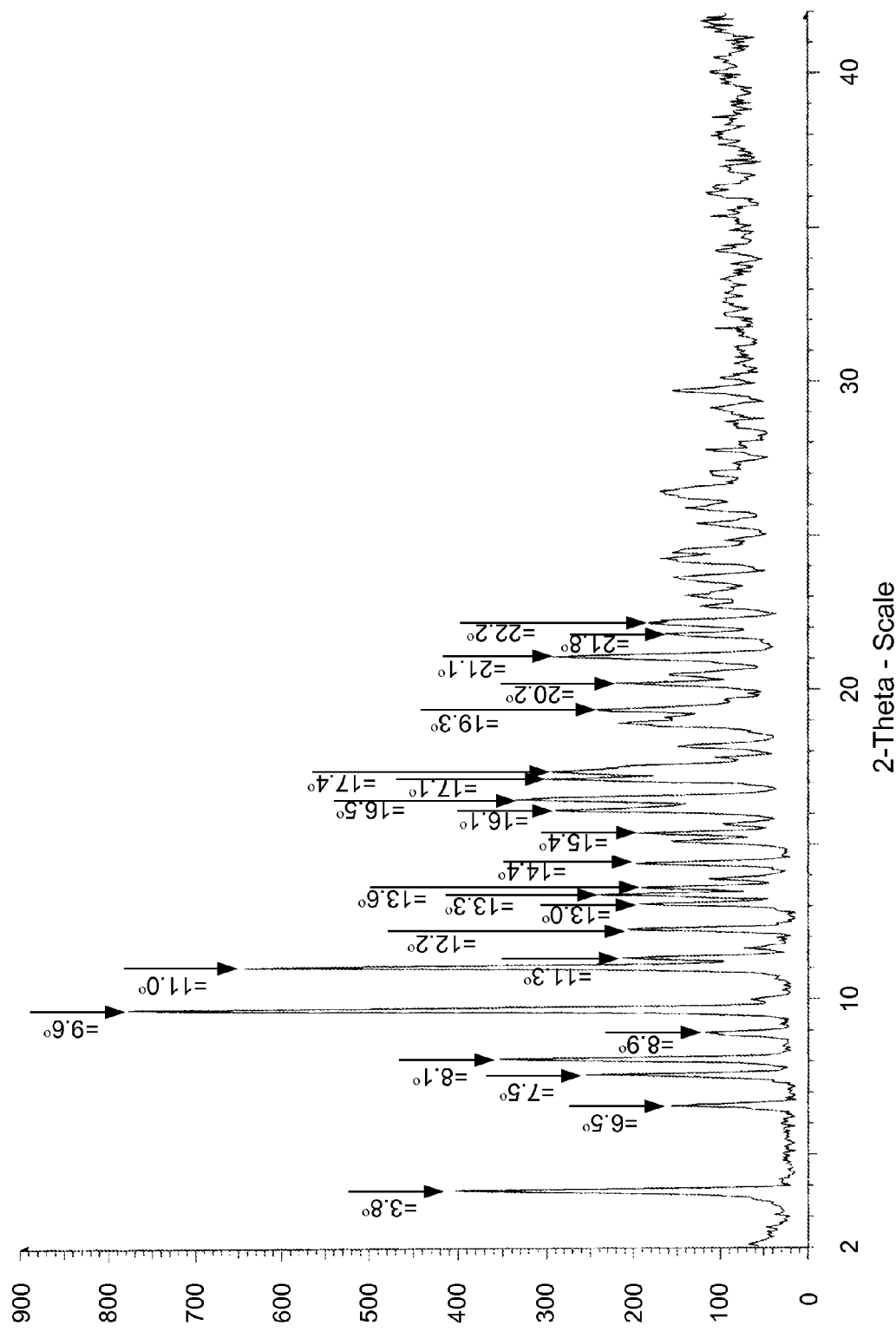
Fig. 1d  XRPD of Polymorph IV

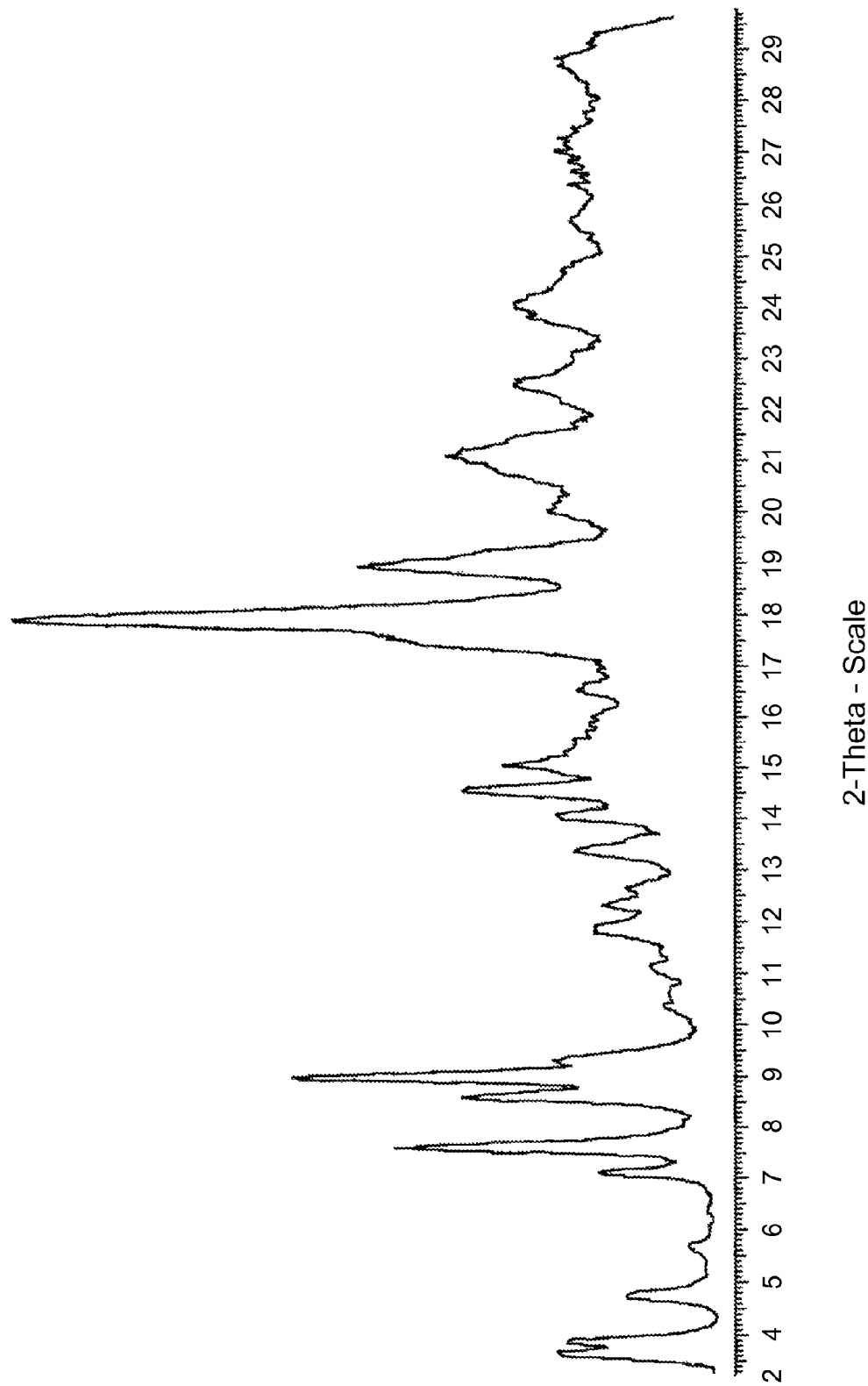
Fig. 1e  XRPD of Polymorph V

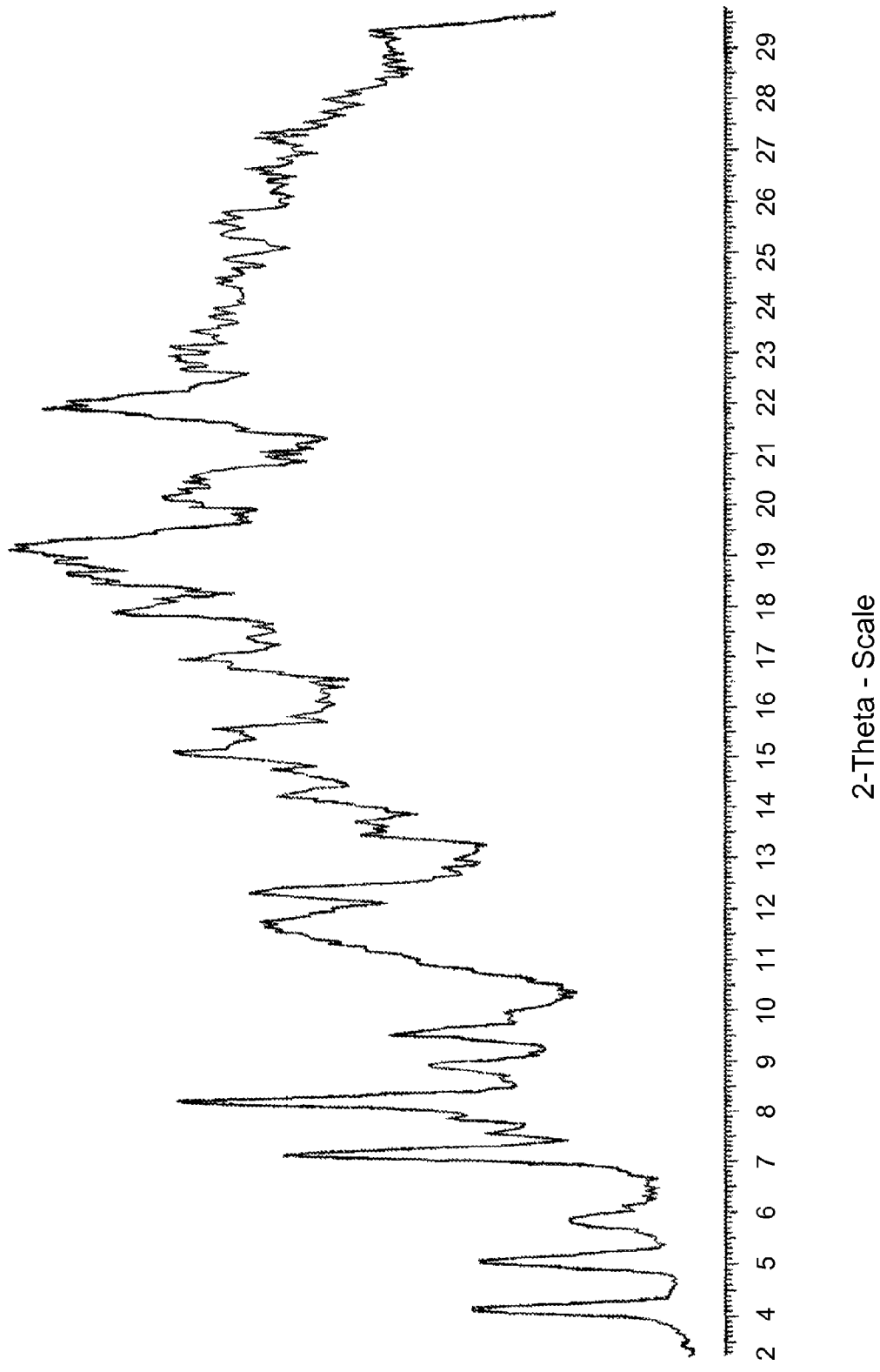

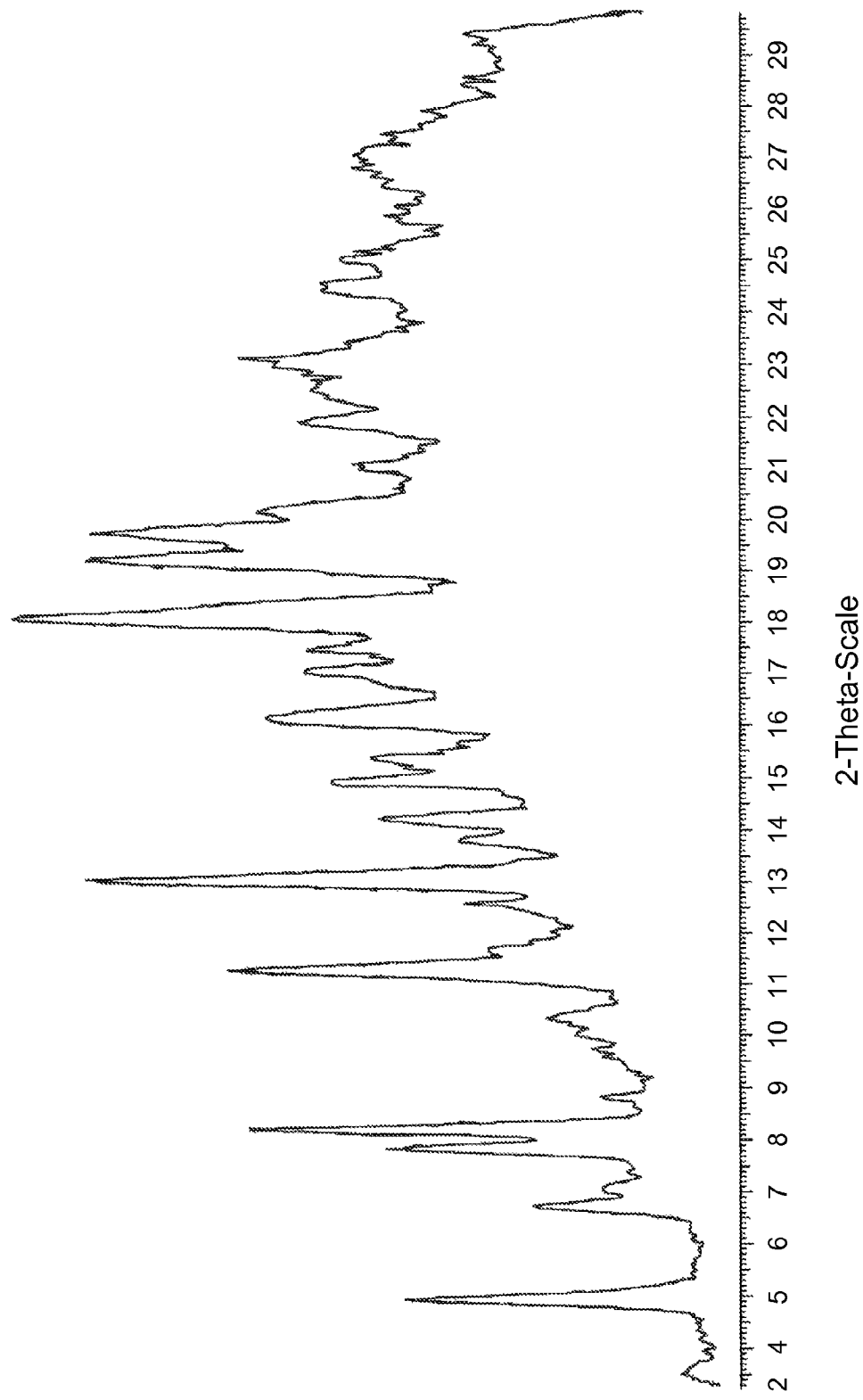
Fig. 1g  XRPD of Polymorph VII

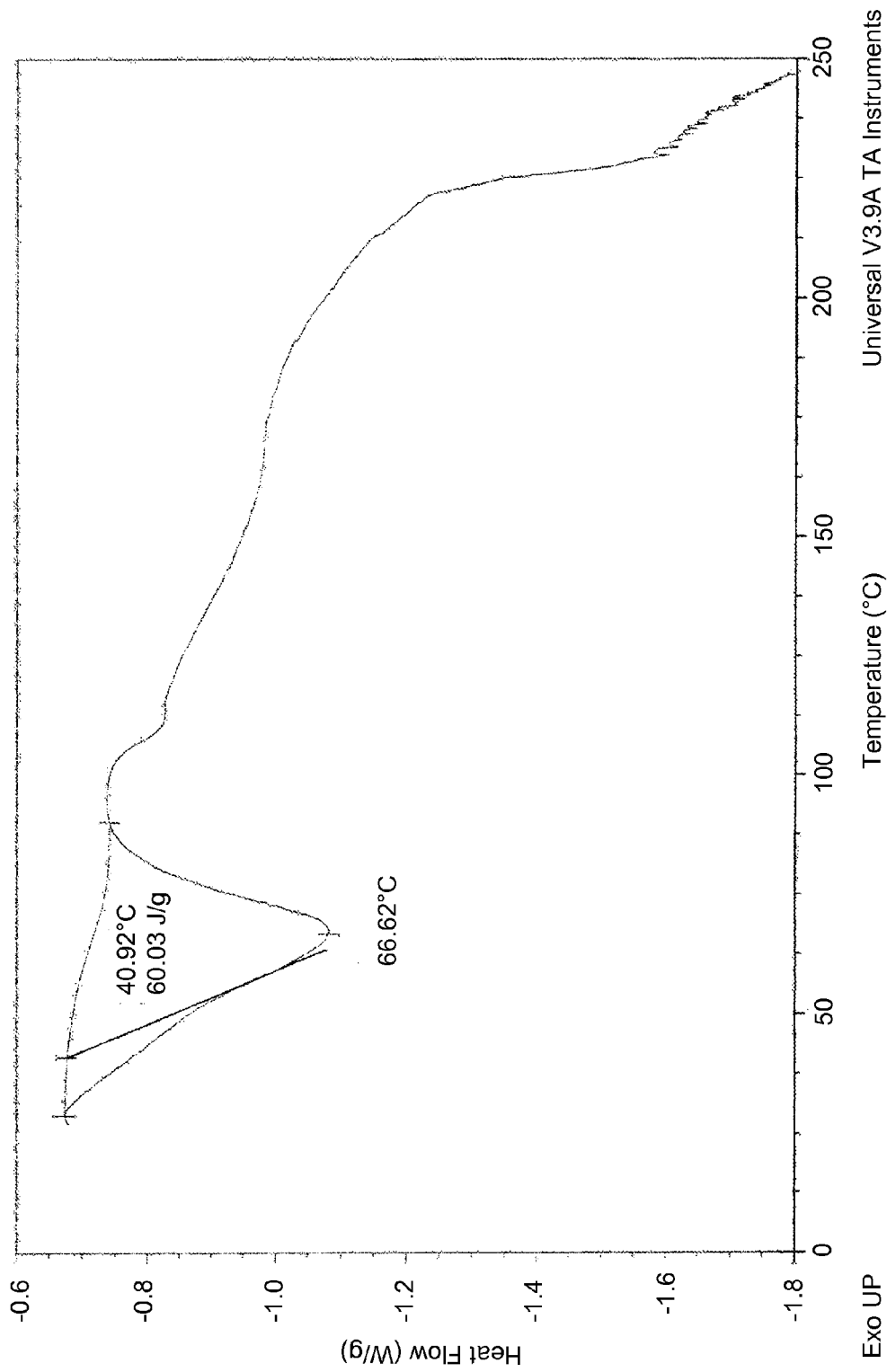
Fig. 2a  DSC of Polymorph I

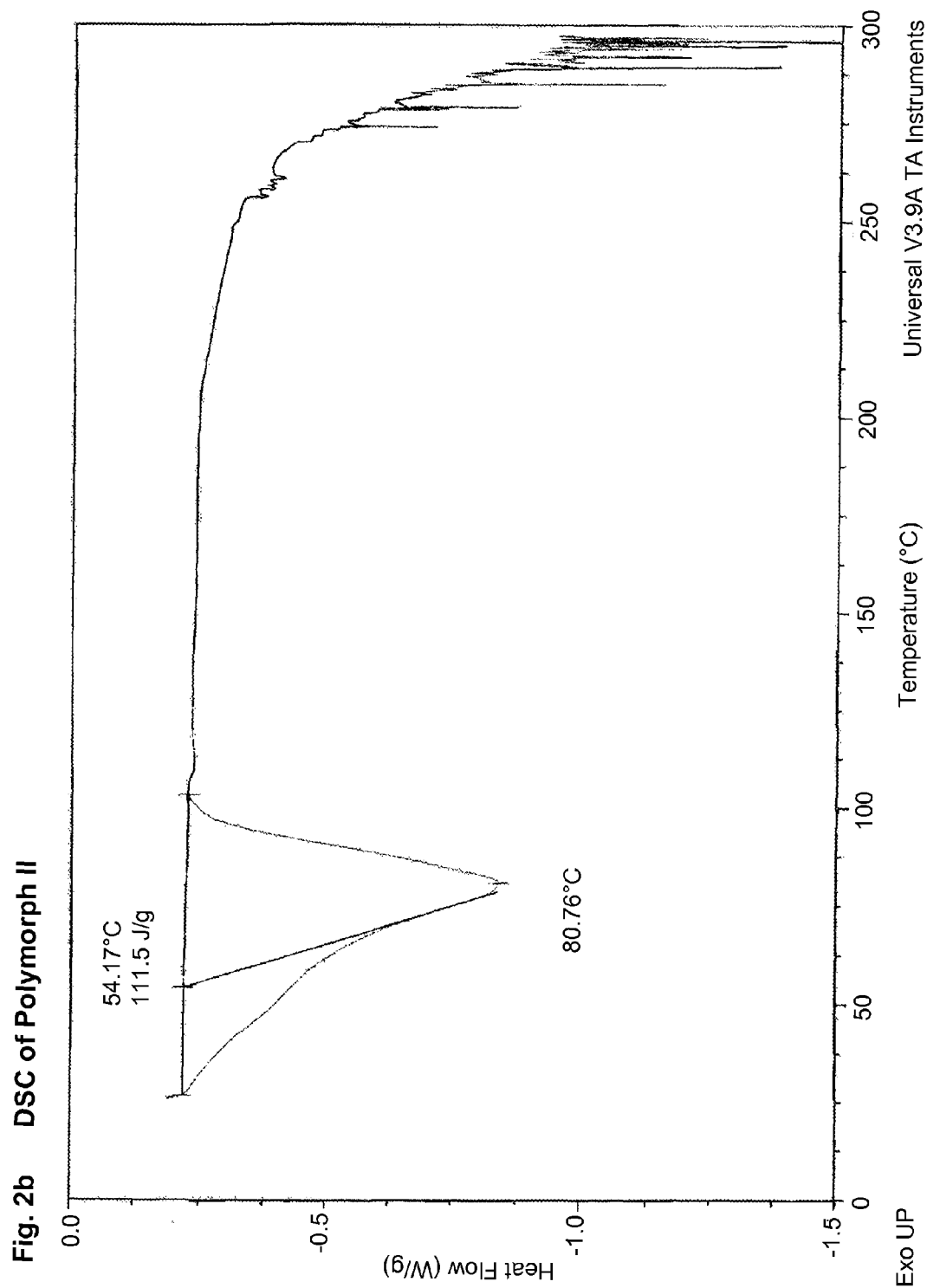
Fig. 2b  DSC of Polymorph II

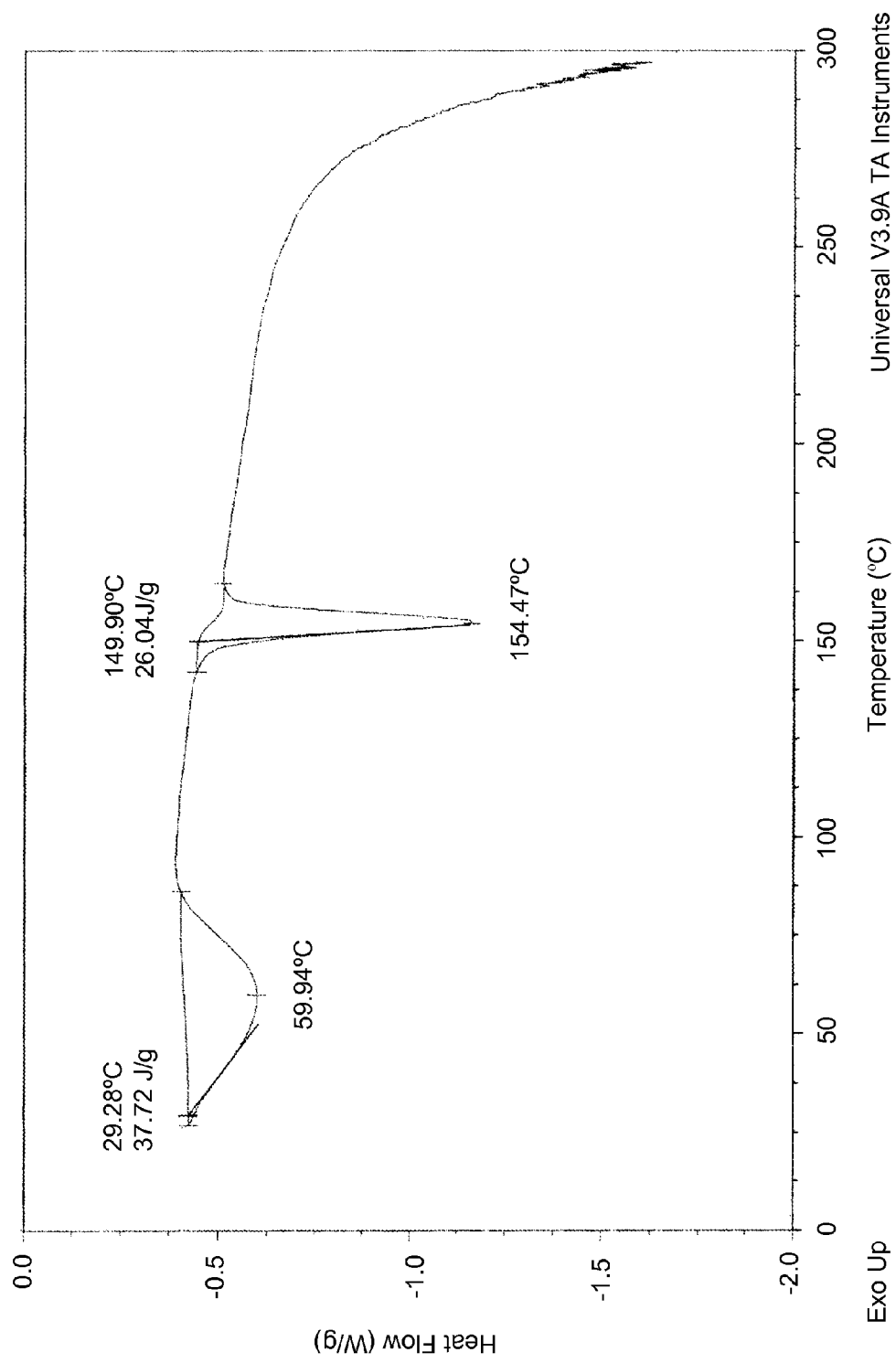
Fig. 2c  DSC of Polymorph IV

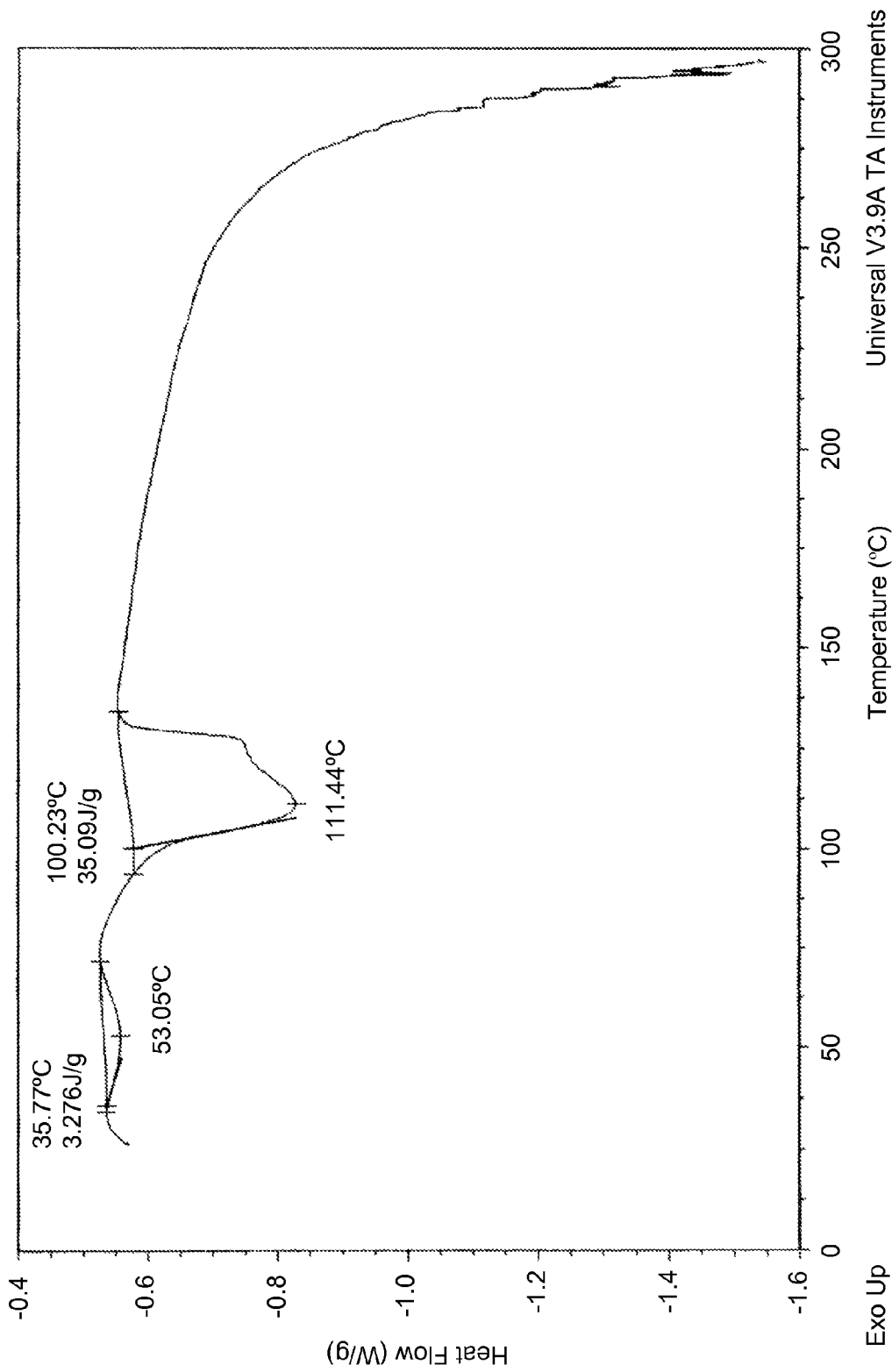
Fig. 2d  DSC of Polymorph V

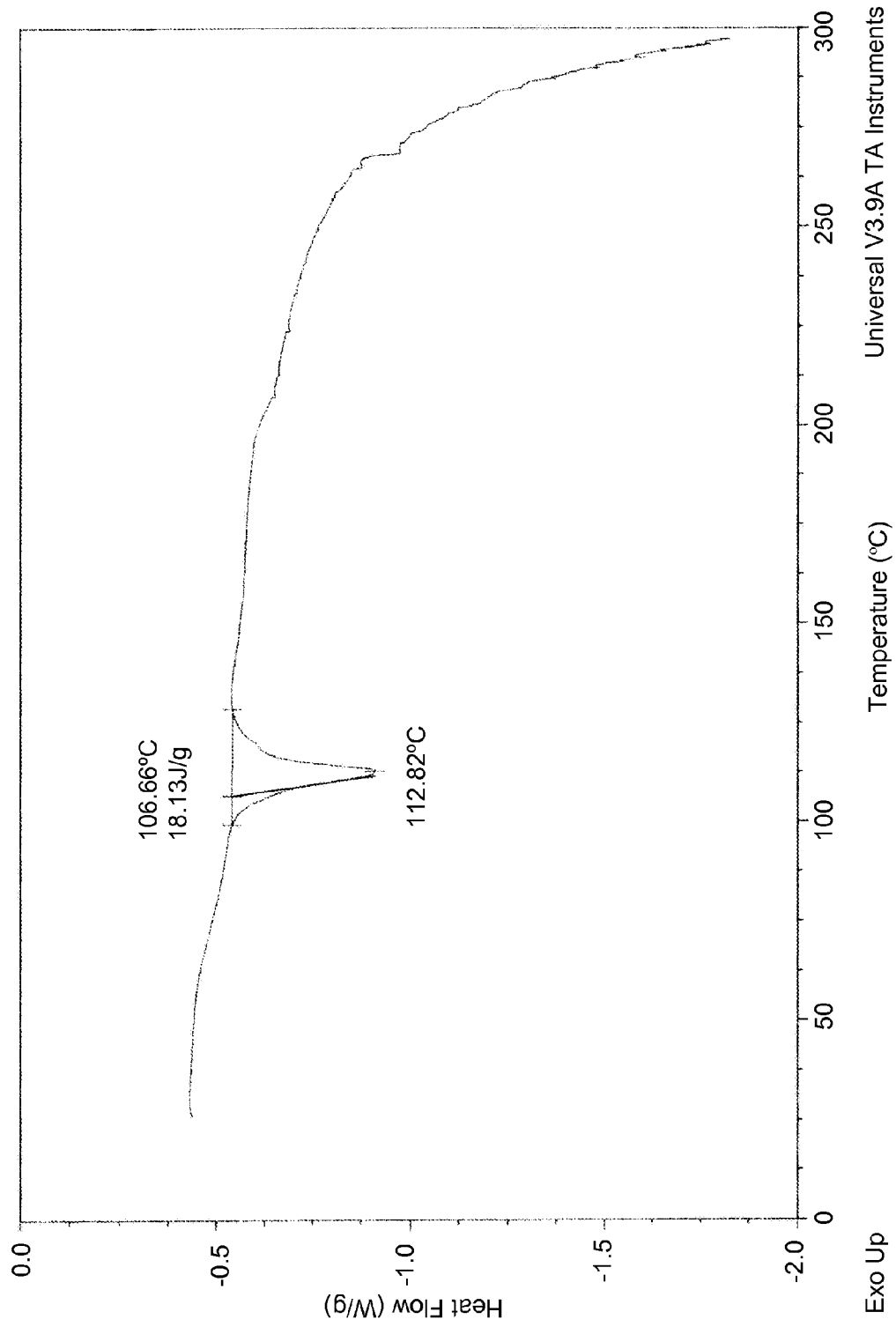
Fig. 2e   DSC of Polymorph VI (EtOAc form)

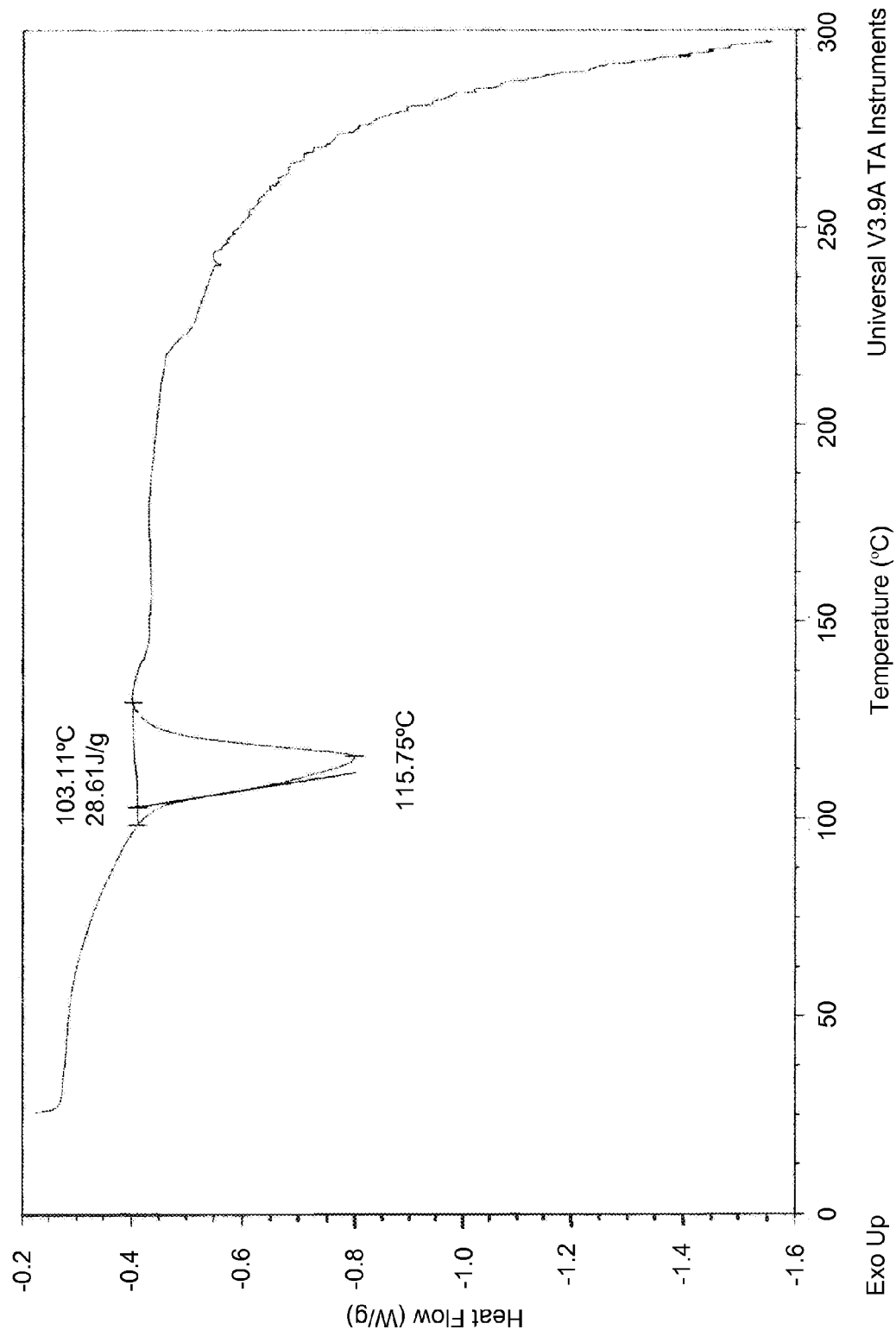
Fig. 2f  DSC of Polymorph VII

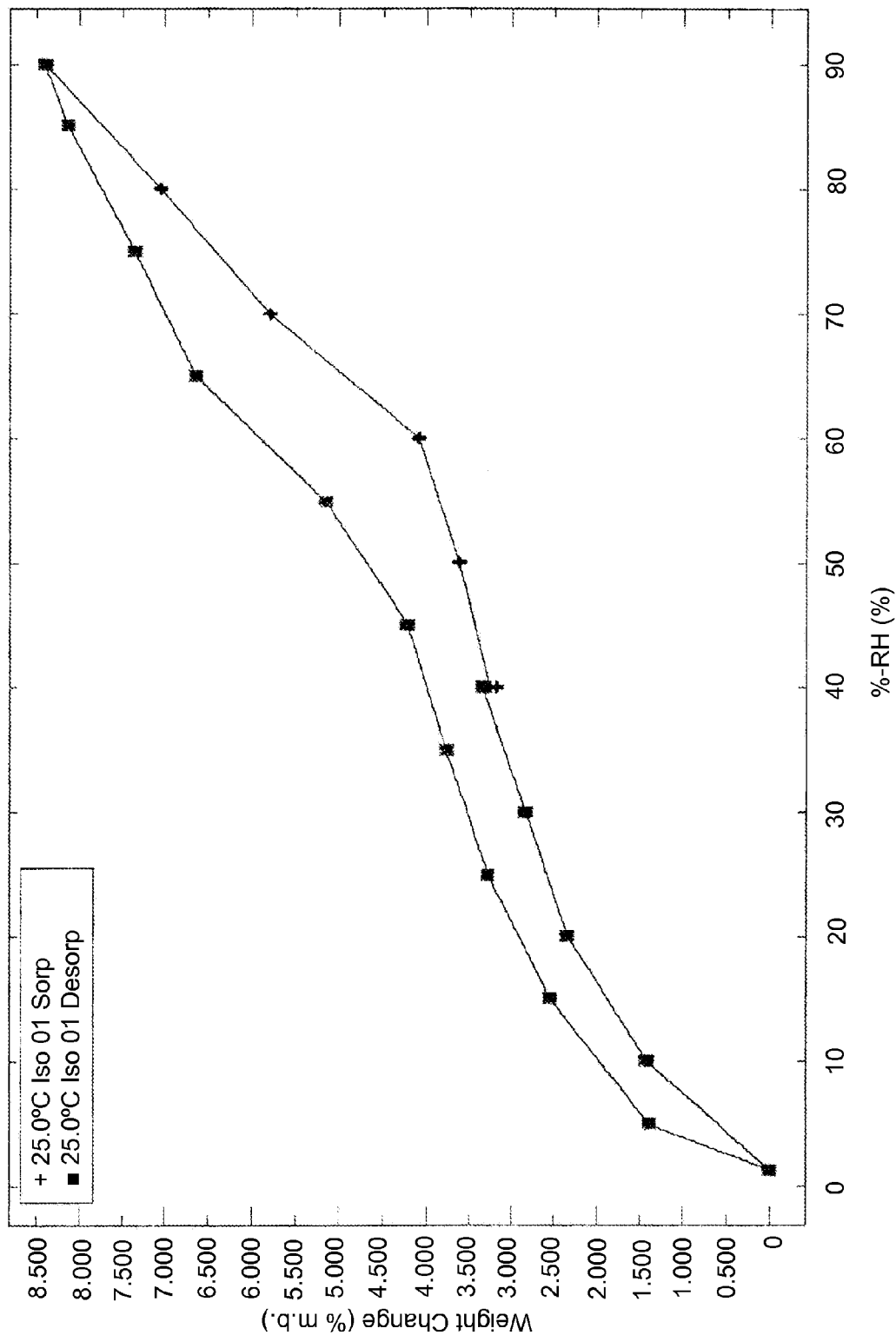
Fig. 3a  GVS of Polymorph I

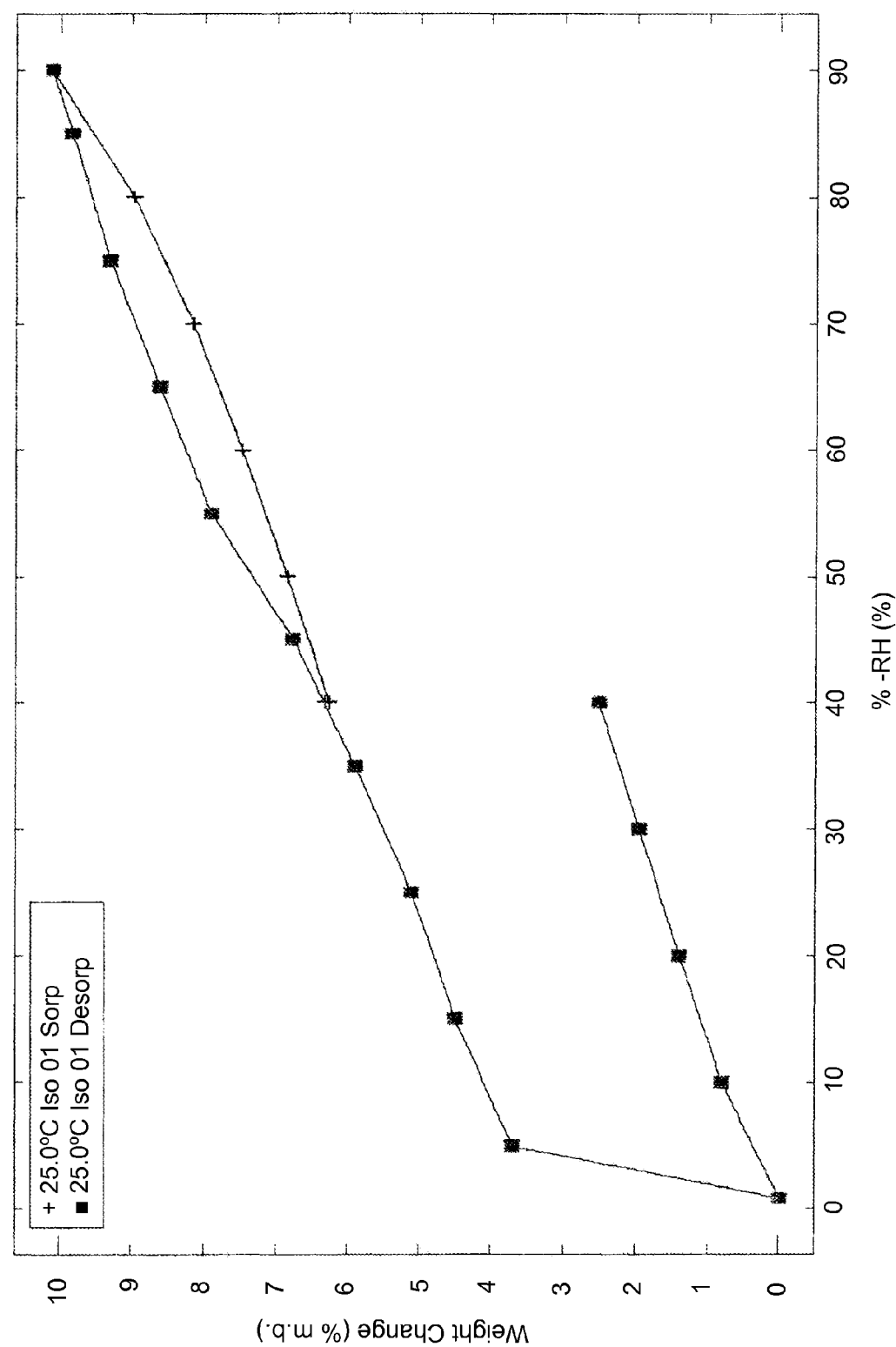
Fig. 3b  GVS of Polymorph II

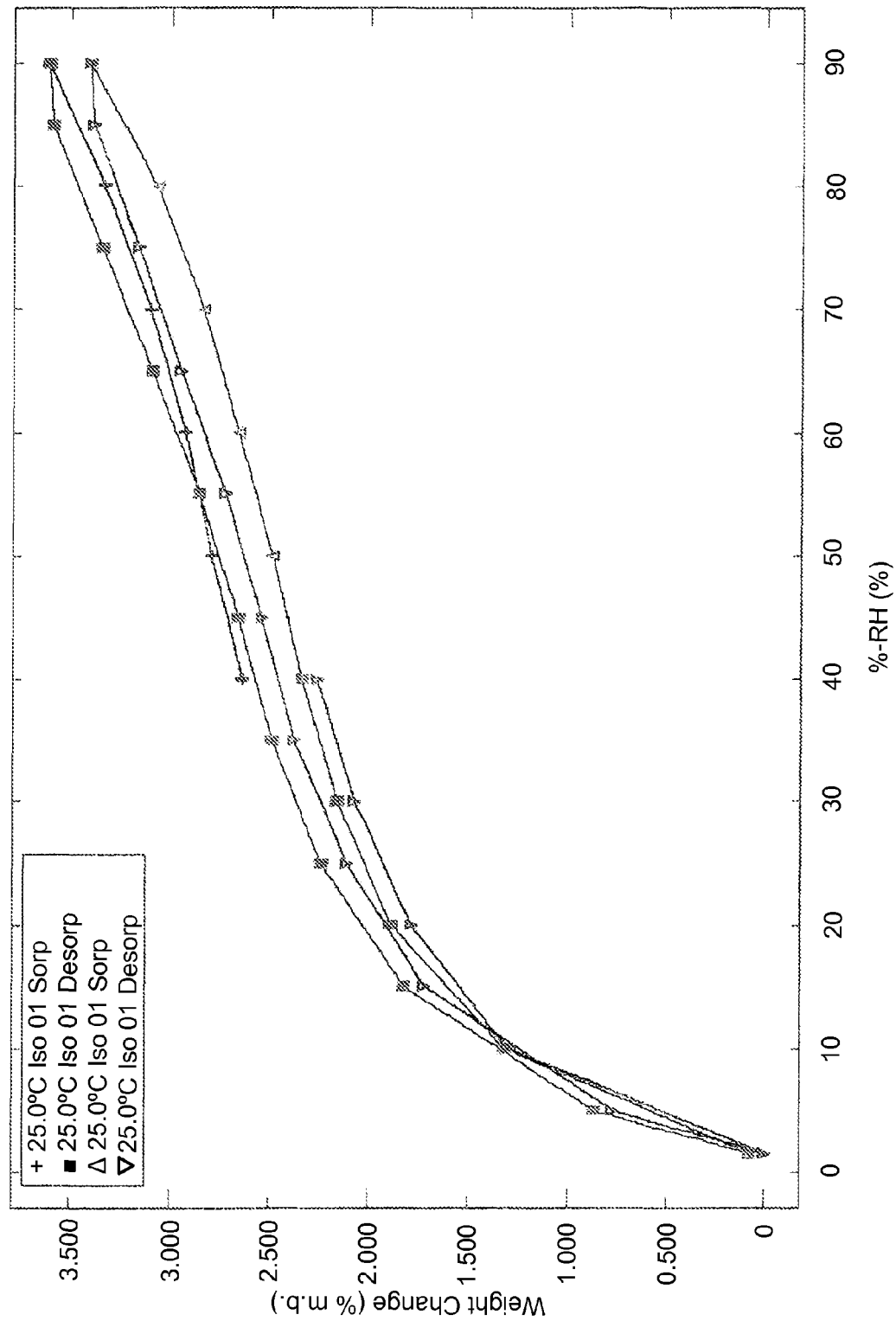
Fig. 3c  GVS of Polymorph IV

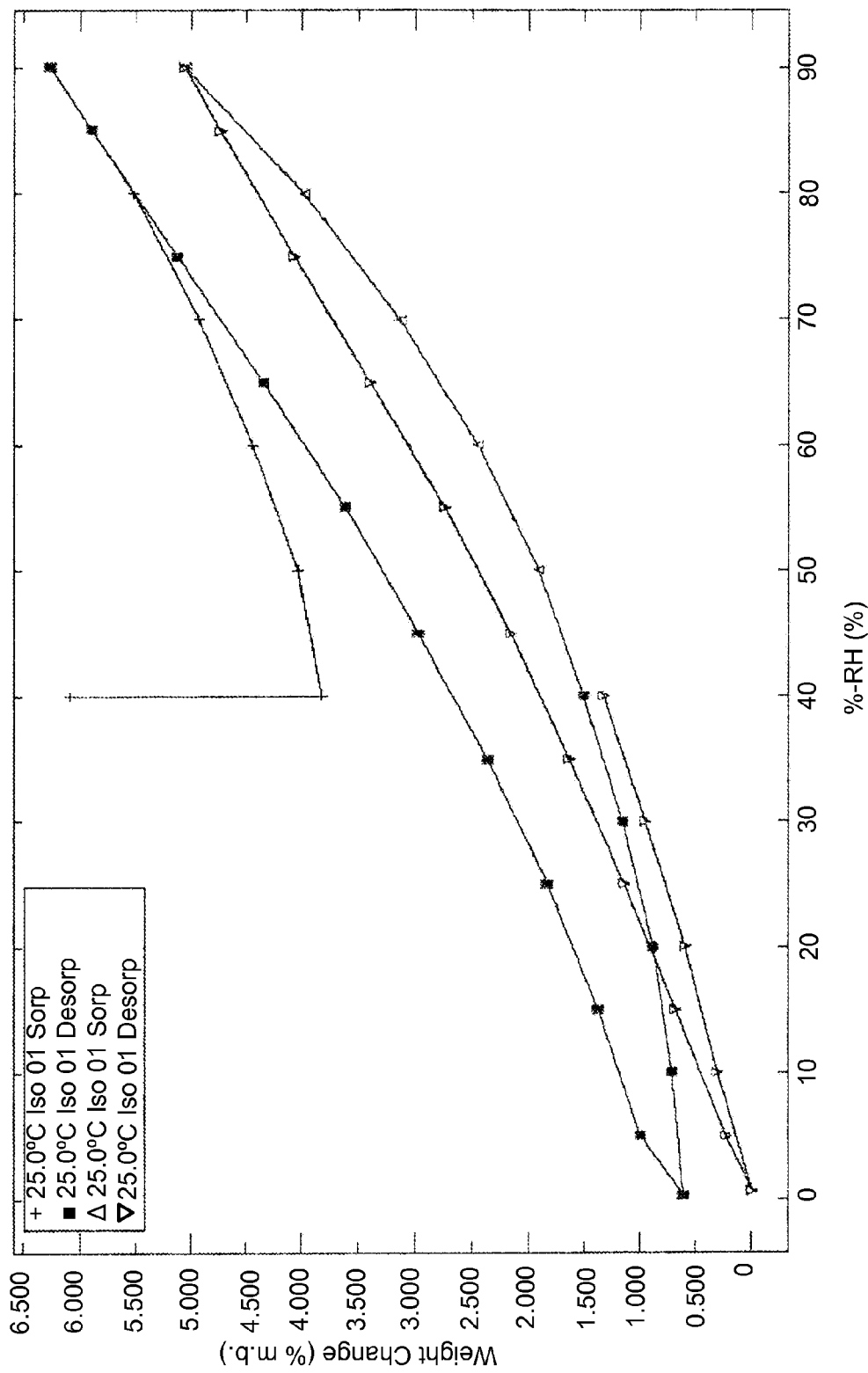
Fig. 3d  GVS of Polymorph IV (EtOCAc form)

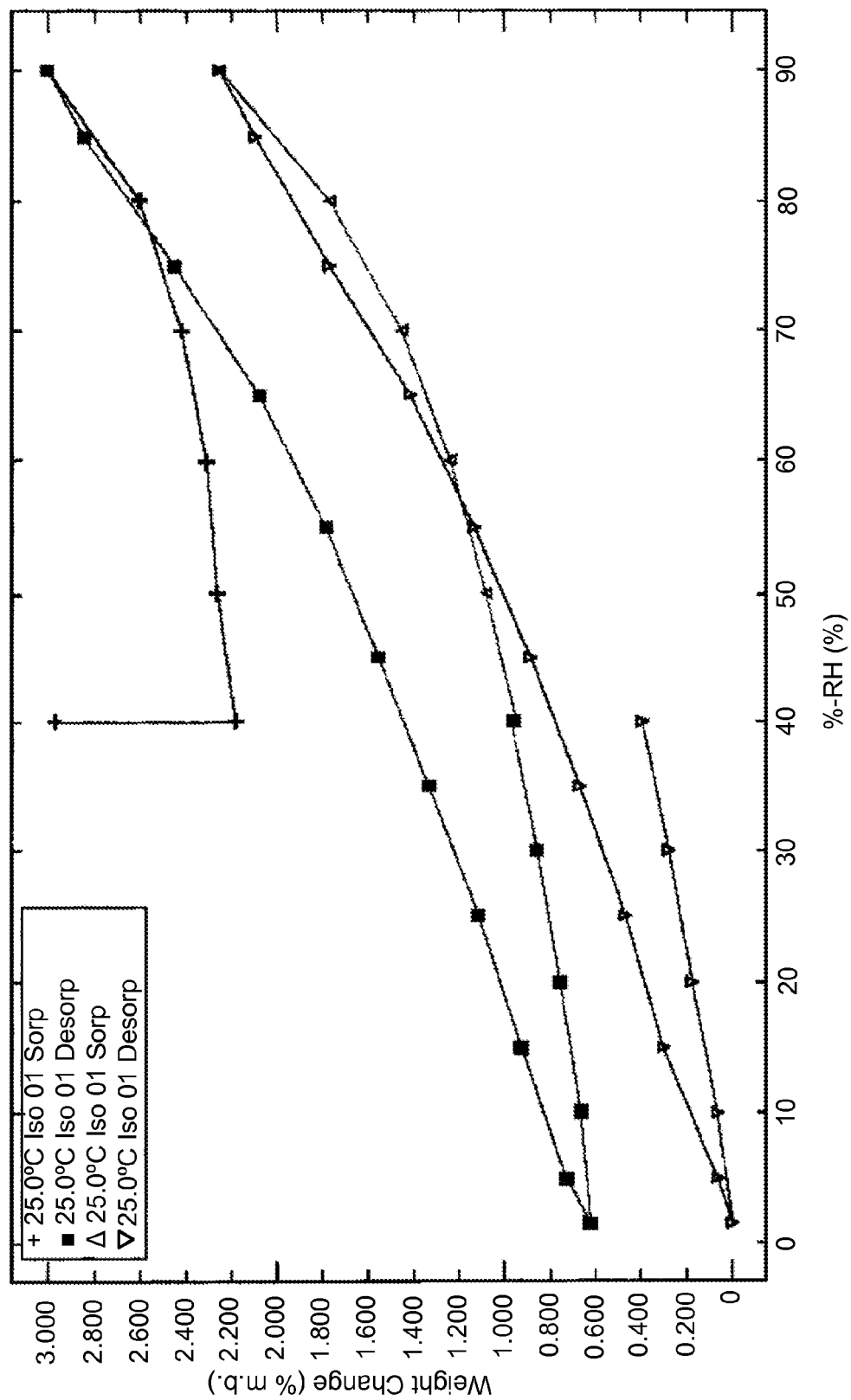
Fig. 3e  GVS of Polymorph IV

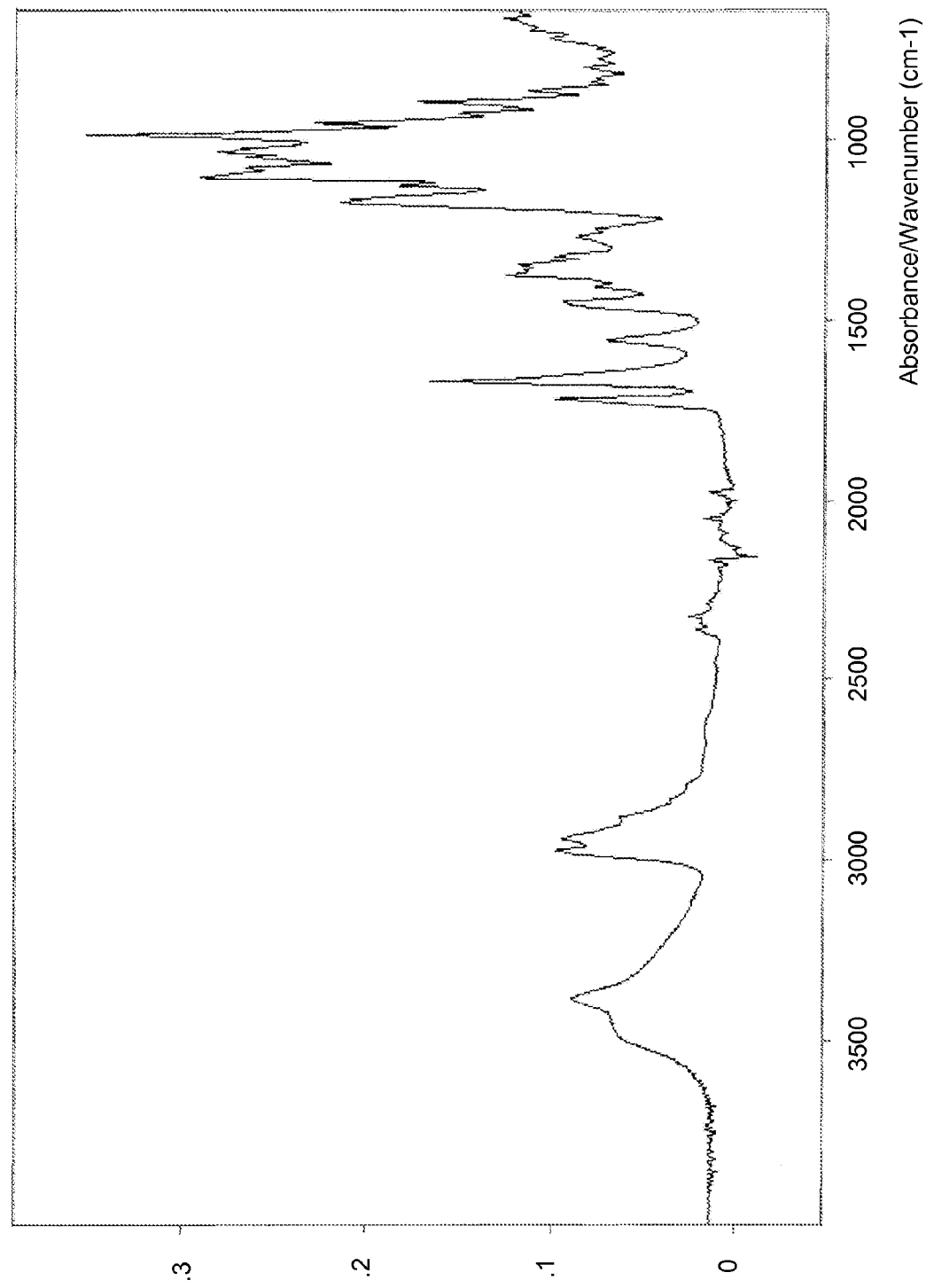
Fig. 5a   FT-IR spectrum for Polymorph IV

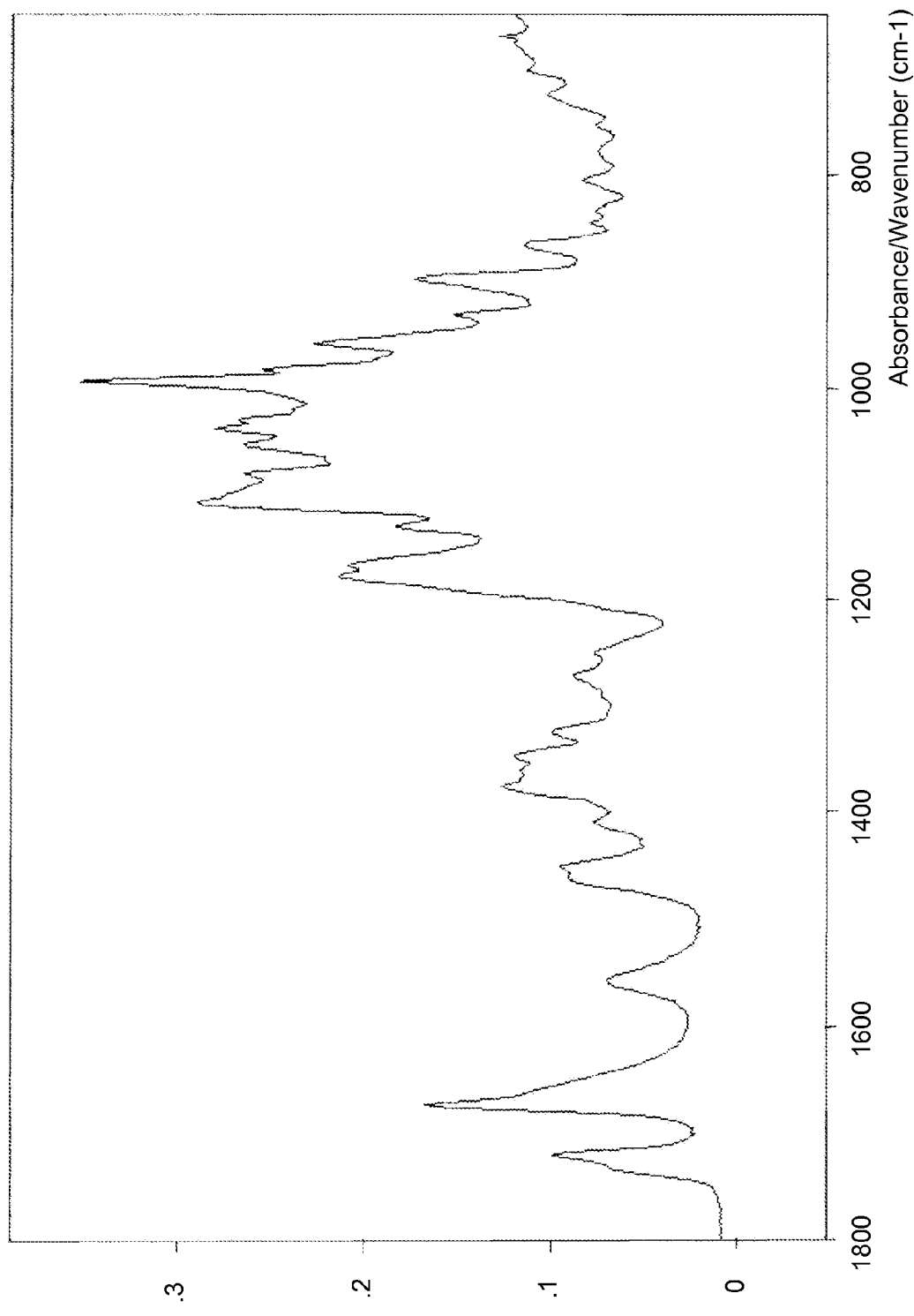
Fig. 5b  FT-IR spectrum for Polymorph IV

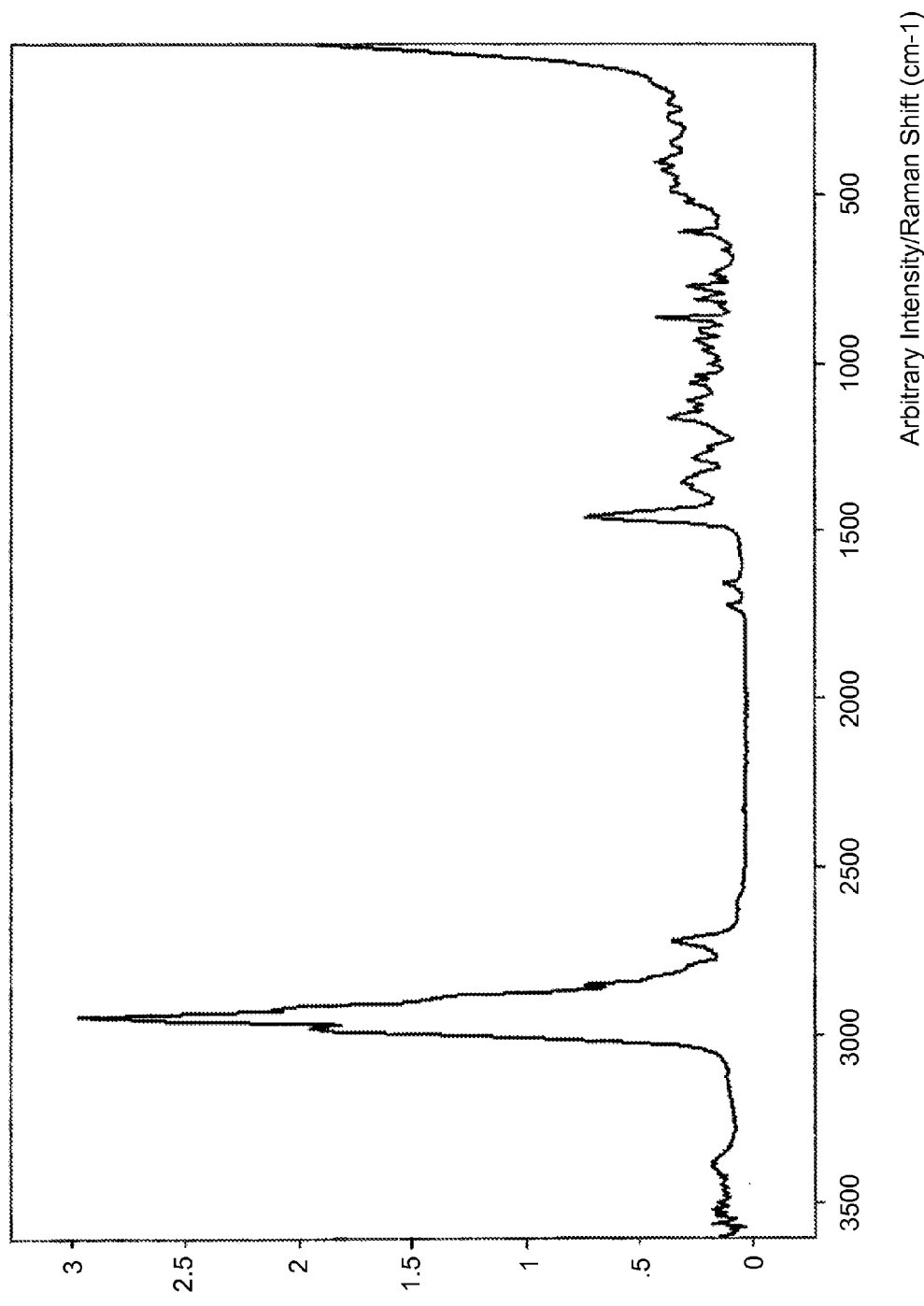
Fig. 6  FT-Raman spectrum for Polymorph IV

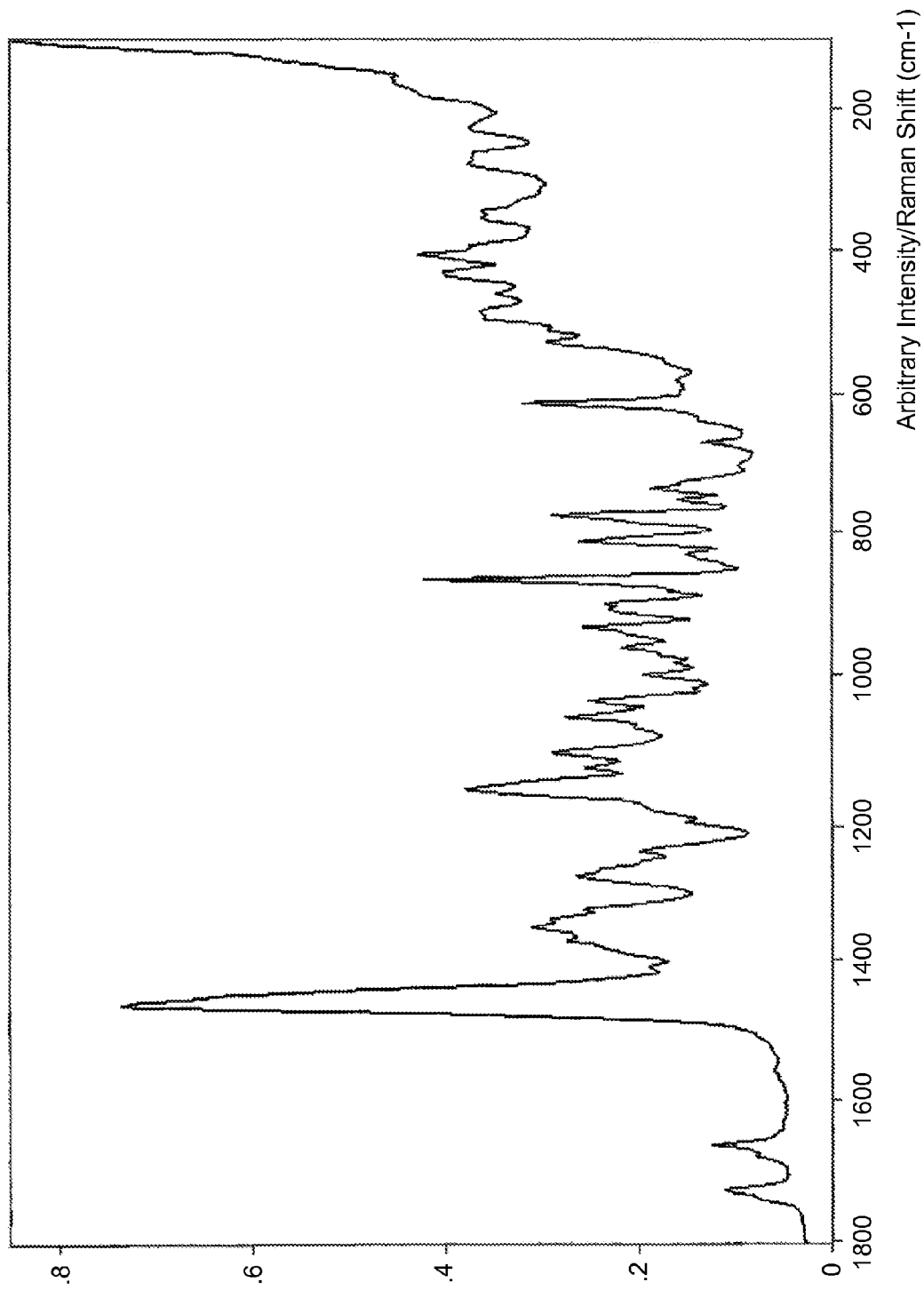
Fig. 6 (cont'd) FT-Raman spectrum for Polymorph IV

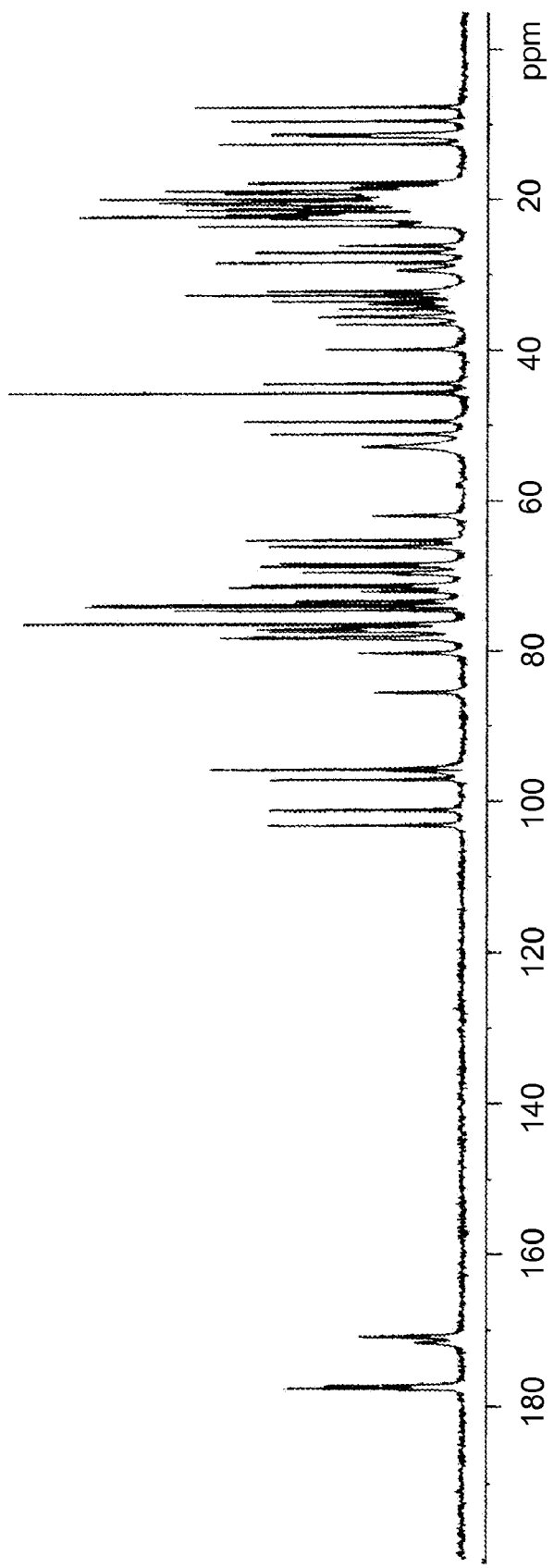
Fig. 7  $^{13}$C solid state NMR spectrum of Polymorph IV

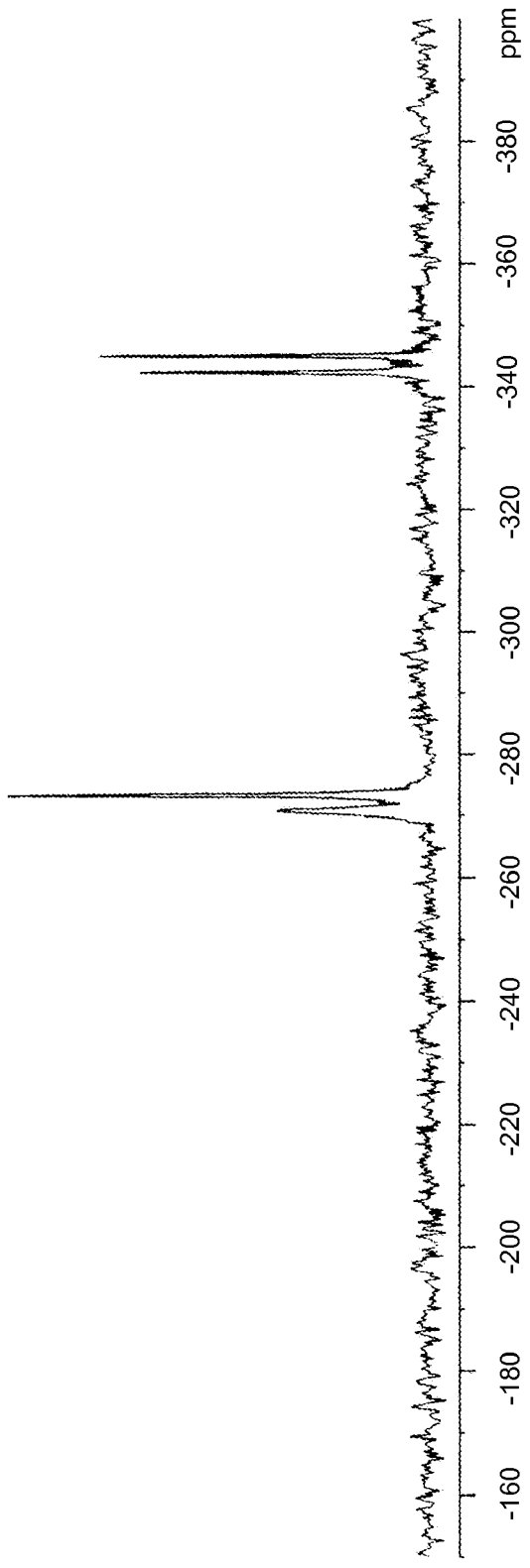
Fig. 8    $^{15}$N solid state NMR spectrum of Polymorph IV

MOTILIDE POLYMORPHS

This application is a continuation of U.S. Ser. No. 11/987,810, filed Dec. 4, 2007, which claims priority to U.S. Ser. No. 60/873,101, filed Dec. 5, 2006. Both prior applications are hereby incorporated by reference in their entirety.

Kosan Biosciences, Inc. and Pharmorphix Ltd. are partners to a joint research agreement.

This invention relates to polymorphs of a motilide and methods for the preparation and use of such polymorphs.

BACKGROUND OF THE INVENTION

Gastrointestinal ("GI") motility regulates the orderly movement of ingested material through the gut to ensure adequate absorption of nutrients, electrolytes, and fluids. Proper transit of the GI contents through the esophagus, stomach, small intestine, and colon depends on regional control of intraluminal pressure and several sphincters, which regulate their forward movement and prevent back-flow. The normal GI motility pattern may be impaired by a variety of circumstances, including disease and surgery.

GI motility disorders include gastroparesis and gastroesophageal reflux disease ("GERDn"). Gastroparesis, whose symptoms include stomach upset, heartburn, nausea, and vomiting, is the delayed emptying of stomach contents. GERD refers to the varied clinical manifestations of the reflux of stomach and duodenal contents into the esophagus. The most common symptoms are heartburn and dysphasia, with blood loss from esophageal erosion also known to occur. Other examples of GI disorders in which impaired GI motility is implicated include anorexia, gall bladder stasis, postoperative paralytic ileus, scleroderma, intestinal pseudo-obstruction, irritable bowel syndrome, gastritis, emesis, and chronic constipation (colonic inertia).

Motilin is a 22-amino acid peptide hormone secreted by endocrine cells in the intestinal mucosa. Its binding to the motilin receptor in the GI tract stimulates GI motility. The administration of therapeutic agents that act as motilin agonists ("prokinetic agents") has been proposed as a treatment for GI disorders.

The erythromycins are a family of macrolide antibiotics made by the fermentation of the actinomycetes *Saccharopolyspora erythraea*. Erythromycin A, a commonly used antibiotic, is the most abundant and important member of the family.

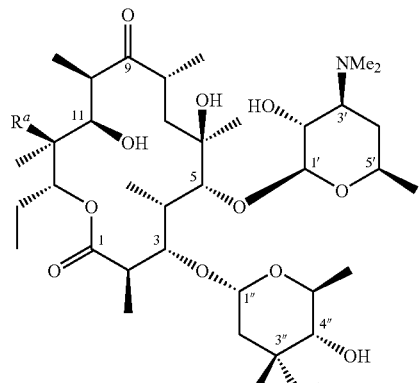

| (1) | Erythromycin A | $R^a$ = OH, $R^b$ = Me |
| (2) | Erythromycin B | $R^a$ = H, $R^b$ = Me |
| (3) | Erythromycin C | $R^a$ = OH, $R^b$ = H |
| (4) | Erythromycin D | $R^a$ = H, $R^b$ = H |

The side effects of erythromycin A include nausea, vomiting, and abdominal discomfort. These effects have been traced to motilin agonist activity in erythromycin A (1) and, more so, its initial acid-catalyzed degradation product (5). (The secondary degradation product, spiroketal (6), is inactive.)

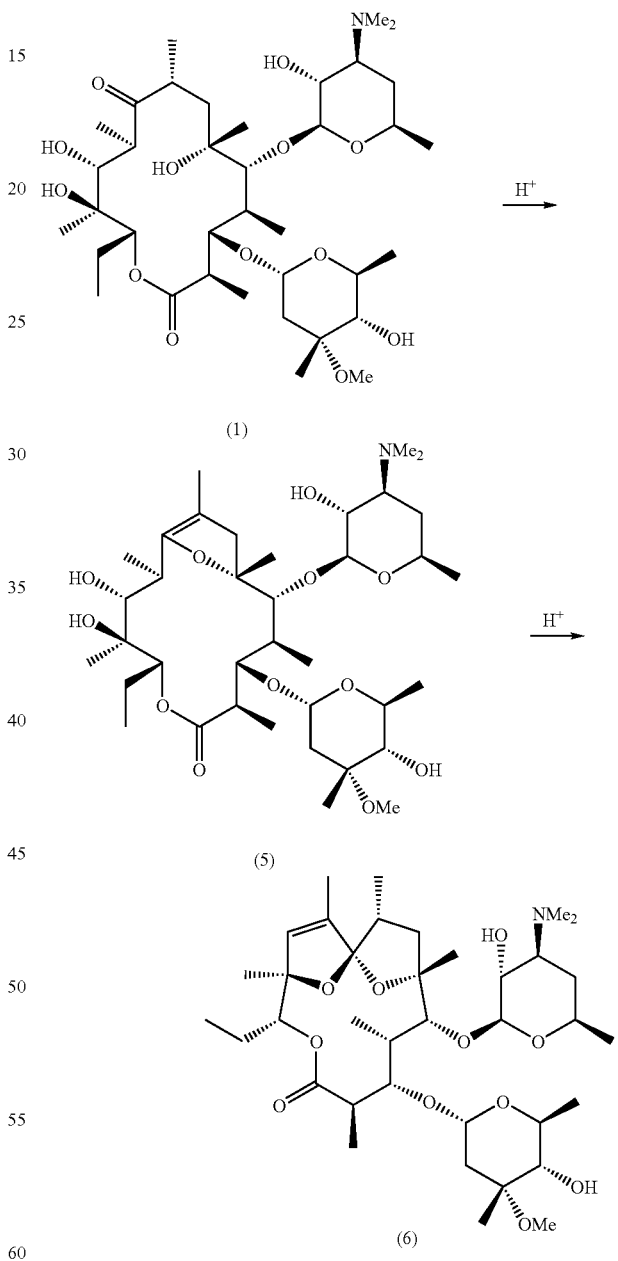

Spurred by the discovery of motilin agonist activity in erythromycin A and degradation product 5, researchers have endeavored to discover new motilides, as macrolides with prokinetic activity are called. Much of the research has centered on generating new erythromycin analogs, either via post-fermentation chemical transformation of a naturally produced erythromycin or via modification (including genetic engineering) of the fermentation process. Illustrative disclosures relating to motilides include: Omura et al., U.S. Pat. No. 5,008,249 (1991) and U.S. Pat. No. 5,175,150 (1992); Harada et al., U.S. Pat. No. 5,470,961 (1995); Freiberg et al., U.S. Pat. No. 5,523,401 (1996); U.S. Pat. No. 5,523,418 (1996); U.S. Pat. No. 5,538,961 (1996); and U.S. Pat. No. 5,554,605 (1996); Lartey et al., U.S. Pat. No. 5,578,579 (1996); U.S. Pat. No. 5,654,411 (1997); U.S. Pat. No. 5,712,253 (1998); and U.S. Pat. No. 5,834,438 (1998); Koga et al., U.S. Pat. No. 5,658,888 (1997); Miura et al., U.S. Pat. No. 5,959,088 (1998); Premchandran et al., U.S. Pat. No. 5,922,849 (1999); Keyes et al., U.S. Pat. No. 6,084,079 (2000); Ashley et al., US 2002/0025936 A1 (2002); Ashley et al., US 2002/0094962 A1 (2002); Carreras et al., US 2002/0192709 A1 (2002); Ito et al., JP 60-218321 (1985) (corresponding Chemical Abstracts abstract no. 104:82047); Santi et al., US 2004/138150 A1 (2004); Carreras et al., US 2005/0113319 A1 (2005); Carreras et al., US 2005/0119195 A1 (2005); Liu et al., US 2005/0256064 A1 (2005); Omura et al., *J. Antibiotics* 1985, 38, 1631-2; Faghih et al., *Biorg. & Med. Chem. Lett.*, 1998, 8, 805-810; Faghih et al., *J. Med. Chem.*, 1998, 41, 3402-3408; Faghih et al., Synlett., July 1998, 751; and Lartey et al., *J. Med. Chem.*, 1995, 38, 1793-1798. The disclosures of all of foregoing documents are incorporated herein by reference.

Also potentially pertinent are other erythromycin scaffold compounds, even where not designed to be motilin agonists, illustrative disclosures being: Krowicki et al., U.S. Pat. No. 3,855,200 (1974); Radobolja et al., U.S. Pat. No. 3,939,144 (1976); Kobrehel et al., U.S. Pat. No. 3,983,103 (1976); Toscano, U.S. Pat. No. 4,588,712 (1986); Agouridas et al., U.S. Pat. No. 5,444,051 (1995); Agouridas et al., U.S. Pat. No. 5,561,118 (1996); Agouridas et al., U.S. Pat. No. 5,770,579 (1998); Asaka et al., U.S. Pat. No. 6,169,168 B1 (2001); Kobrehel et al., DE 2,402,200 (1974); Pliva Pharmaceuticals, GB 1,416,281 (1975); Pliva Pharmaceuticals, GB 1,461,032 (1977); Asaga et al., JP 2002/241391 (2002); Ryden et al., *J. Med. Chemistry*, 1973, 16 (9), 1059-1060; Naperty et al., *Roczniki Chemii*, 1977, 51 (6), 1207-10; Kobrehel et al., *Eur. J. Med. Chemistry*, 1978, 13 (1), 83-7; Egan et al., *J. Antibiotics*, 1978, 31 (1), 55-62; Matijasevic et al., *Croatica Chemica Acta*, 1980, 53 (3), 519-24; Radobolja et al., *Croatica Chemica Acta*, 1985, 58 (2), 219-25; Hunt et al., *J. Antibiotics*, 1989, 42 (2), 293-298; Myles et al., *J. Org. Chem.*, 1990, 55, 1636-1648. The disclosures of all of foregoing documents are incorporated herein by reference.

Those skilled in the art will understand that a number of parameters are relevant to the development of motilides. Firstly, the evolution of the erythromycin scaffold in the natural producing organisms has been driven by antibacterial efficacy and not by prokinetic efficacy. Therefore, considerable room remains for optimization of the structure-activity relationship for motilin agonists. Secondly, it is in fact undesirable for a motilide to possess antibacterial activity. The GI tract is host to a large population of bacteria, whose exposure to a motilide having antibacterial activity may induce the development in them of resistance to erythromycin antibiotics. Or, a motilide having anti-bacterial activity may kill beneficial gut bacteria. Thus, a motilide desirably has enhanced prokinetic activity engineered in and antibacterial activity engineered out. Thirdly, a drawback commonly found among motilides evaluated to date is their propensity to desensitize the motilide receptor, meaning that, after the initial dose, subsequent doses of a motilide elicit a weaker or no response (tachyphylaxis). Fourthly, stability and bioavailability are concerns—witness the ready degradation of erythromycin A in the stomach and the lack of activity of its secondary degradation product. Fifthly, some compounds in the erythromycin family have been reported to have undesirable pro-arrhythmic effects, including the prolongation of the QT interval and the induction of ventricular arrhythmias. Limiting these effects to an acceptable level is desirable. Thus, there exists a continuing need to develop new motilides, balancing the various different performance requirements.

Liu et al., US 2006/0270616 A1 (2006), incorporated herein by reference (hereinafter the "Liu '616 Application"), discloses a family of motilides represented by the general formula I, wherein $R^A$, $R^B$, $R^C$, $R^D$, and $R^E$ are structural variables. A specific compound disclosed there is compound (Ia), which possesses an attractive balance of properties for a motilide.

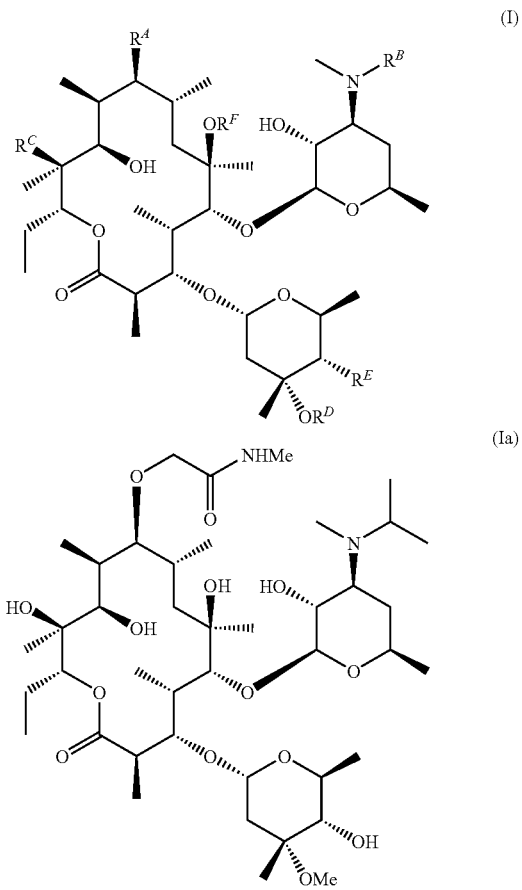

Once a compound has been selected for development as a possible clinical candidate, consideration must be given to formulating it in an appropriate pharmaceutical formulation. In turn, this means consideration must be given to the possible existence of polymorphs. If polymorphs exist, they may differ in their pharmaceutically relevant properties, including solubility, storage stability, hygroscopicity, density, and bioavailability. One polymorph may more or less spontaneously convert to another polymorph during storage. As a result of such conversion, a formulation designed to deliver a particular polymorph may end up containing a different polymorph that is incompatible with the formulation. A hygroscopic polymorph may pick up water during storage, introducing errors into weighing operations and affecting handleability. A preparation procedure designed for use with a particular polymorph may be unsuitable for use with a different polymorph. Even if no interconversion occurs, one polymorph may be easier to formulate than another, making selection of the right polymorph critical. Thus, polymorph choice is an important factor in designing a pharmaceutical formulation. (As used herein, the term "polymorph" includes amorphous forms and non-solvated and solvated crystalline forms, as specified in guideline Q6A(2) of the ICH (International Conference on Harmonization of Technical Requirements for Registration of Pharmaceuticals for Human Use)).

SUMMARY OF THE INVENTION

The present invention relates to polymorphs of compound Ia that are especially desirable for use in pharmaceutical formulations.

Compound Ia, when prepared according to the Liu '616 Application, is obtained in a form that is not optimized for formulation development (this form is designated herein as Polymorph I—see Example 3 below). We have discovered additional polymorphs of compound Ia, including one (referred to herein as Polymorph IV) that has improved properties for use in a pharmaceutical formulation. Another polymorph, designated Polymorph II, also has suitable properties for use in a pharmaceutical formulation. Thus, in one embodiment, this invention provides purified polymorph IV of compound Ia. In another embodiment it provides purified polymorph II of compound Ia.

In another embodiment, this invention provides a method for preparing purified Polymorph IV of Compound Ia, comprising subjecting to the polymorph of Compound Ia referred to herein as Polymorph II to plural heating and cooling cycles in the presence of a medium selected from diisopropyl ether ("DIPE") and a $C_5$-$C_7$ alkane or alkene (preferably heptane).

In another embodiment, this invention provides a method for preparing purified Polymorph IV of Compound Ia, comprising preparing an ethyl acetate solution of Compound Ia and adding a $C_5$-$C_7$ alkane or alkene to the solution to cause crystallization of Compound Ia as purified Polymorph IV.

In another embodiment, this invention provides a pharmaceutical formulation comprising a purified Polymorph IV of Compound Ia and a pharmaceutically acceptable excipient.

In another embodiment, this invention provides a pharmaceutical formulation comprising a purified Polymorph II of Compound Ia and a pharmaceutically acceptable excipient.

The invention further provides: a method of treating a disease of impaired gastric motility, comprising administering to a subject in need of such treatment a therapeutically effective amount of a purified Polymorph IV of Compound Ia; a purified Polymorph IV of Compound Ia for use as a medicament; a purified Polymorph IV of Compound Ia for use in the treatment of a disease of impaired gastric motility; the use of a purified Polymorph IV of Compound Ia for the manufacture of a medicament for the treatment of a disease of impaired gastric motility; and a pharmaceutical composition for the treatment of a disease of impaired gastric motility containing a purified Polymorph IV of Compound Ia.

The invention further provides: a method of treating a disease of impaired gastric motility, comprising administering to a subject in need of such treatment a therapeutically effective amount of a purified Polymorph II of Compound Ia; a purified Polymorph II of Compound Ia for use as a medicament; a purified Polymorph II of Compound Ia for use in the treatment of a disease of impaired gastric motility; the use of a purified Polymorph II of Compound Ia for the manufacture of a medicament for the treatment of a disease of impaired gastric motility; and a pharmaceutical composition for the treatment of a disease of impaired gastric motility containing a purified Polymorph II of Compound Ia.

Illustrative examples of disorders which are diseases of impaired gastric motility include (without limitation) gastroparesis, gastroesophageal reflux disease ("GERD"), anorexia, gall bladder stasis, postoperative paralytic ileus, scleroderma, intestinal pseudo-obstruction, irritable bowel syndrome, gastritis, emesis, and chronic constipation (colonic inertia). The polymorphs of the invention are particularly effective in the treatment of GERD.

BRIEF DESCRIPTION OF THE DRAWINGS

FIGS. 1a, 1b, 1c, 1d, 1e, 1f and 1g are representative X-ray powder diffraction ("XRPD") patterns for Polymorphs I, II, III, IV, V, VI (ethyl acetate form), and VII, respectively, of Compound Ia.

FIGS. 2a, 2b, 2c, 2d, 2e and 2f are representative differential scanning calorimetry ("DSC") scans for Polymorphs I, II, IV, V, VI (ethyl acetate form), and VII, respectively, of Compound Ia.

FIGS. 3a, 3b, 3c, 3d, and 3e are representative gravimetric vapor sorption ("GVS") scans for Polymorphs I, II, IV, VI (ethyl acetate form), and VII, respectively, of Compound Ia.

FIG. 5 is a representative FT-IR (fourier transform infra red) scan for Polymorph IV.

FIG. 6 is a representative FT-Raman scan for Polymorph IV.

FIG. 7 is a representative $^{13}$C solid state NMR scan for Polymorph IV.

FIG. 8 is a representative $^{15}$N solid state NMR scan for Polymorph IV.

DETAILED DESCRIPTION OF THE INVENTION

Polymorph I was characterized as a white powder that was largely amorphous, being poorly crystalline by XRPD. It was relatively hygroscopic, showing an 8.5% weight increase between 0 and 90% RH (relative humidity). Thermal analysis showed an endotherm between ambient temperature and 90° C. due to solvent loss. The weight loss accompanying the endotherm was 3.0%, corresponding to 1.4 moles of water. When heated to a temperature between 75 and 100° C., Polymorph I lost crystallinity. Under aqueous conditions Polymorph I converted to a second polymorph, referred to as Polymorph II. These latter two observations militate against the selection of Polymorph I as a polymorph for formulation development. Representative XRPD, DSC, and GVS data for Polymorph I are shown in FIGS. 1a, 2a, and 3a, respectively.

Figure 1B:
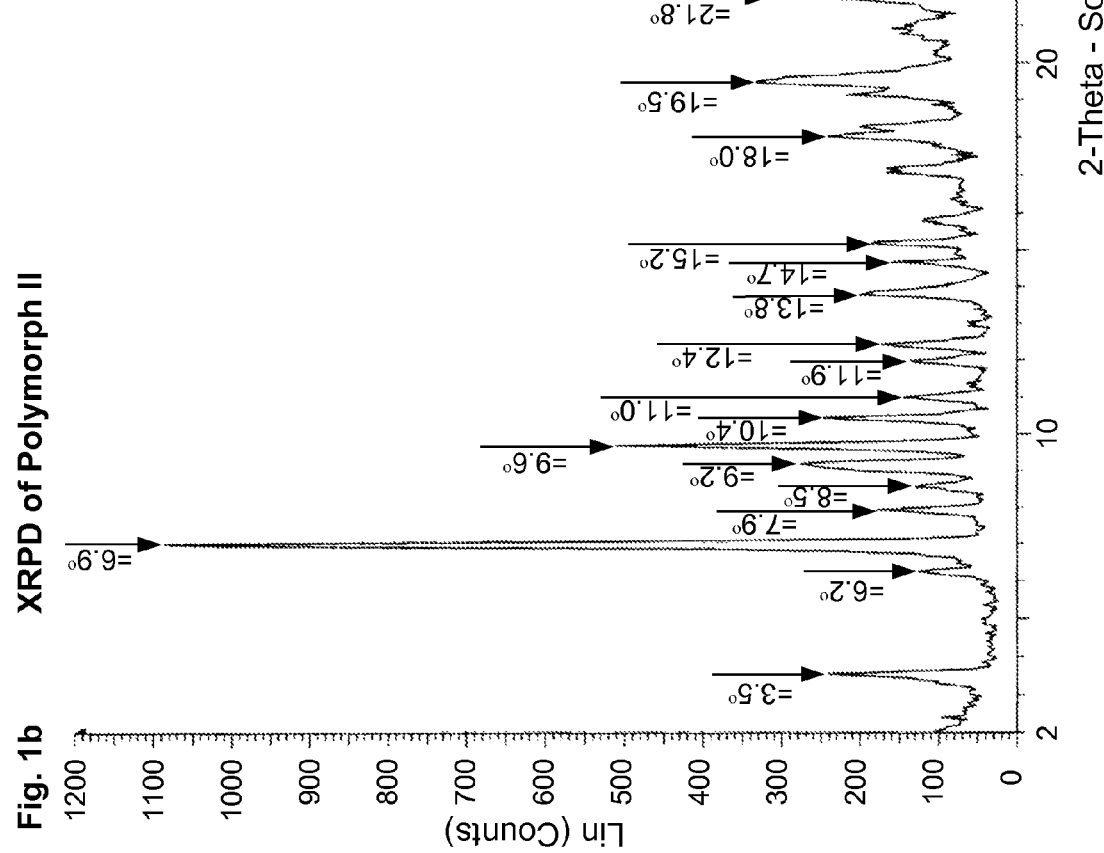
Figure 4:
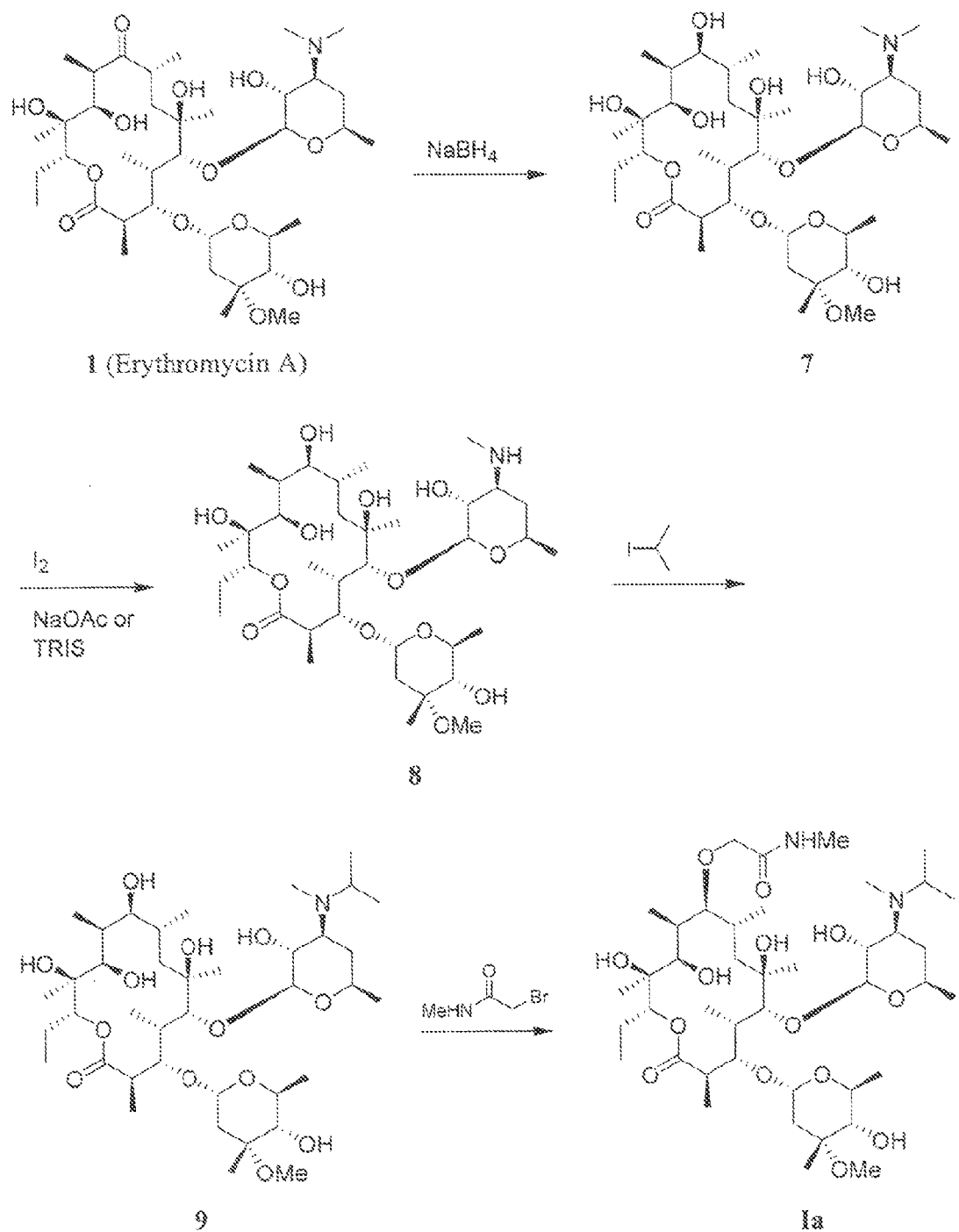
FIG. 4 shows a synthetic scheme for the preparation of compound Ia.

Polymorph II was characterized as a white powder with small particle size (<10 μm) and no discernable morphology. XRPD showed it to be crystalline with some amorphous content. When kept at between 5 and 0% RH, Polymorph II showed a 4% weight loss, equivalent to 2 moles of water per mole of compound (Ia). There was a corresponding loss of crystallinity as evidenced by XRPD re-analysis under ambient conditions, suggesting that Polymorph II is a di-hydrate. Thermal analysis showed a broad endotherm between ambient temperature and 100° C. due to solvent (water) loss. This loss corresponds to a 5.0% weight loss, equivalent to 2.5 moles of water, the additional water content attributable to Polymorph II's being hygroscopic. There was a loss of crystallinity between 50 and 75° C. Polymorph II also loses crystallinity during vacuum drying at 30° C. for 72 h. Representative XRPD, DSC, and GVS data for Polymorph II are shown in FIGS. 1b, 2b, and 3b, respectively.

Polymorph IV was characterized as a white powder with particle size up to 50 μm and acicular morphology. It was crystalline by XRPD. Its aqueous solubility was 0.77 mg/mL. At a purity level of 97.9%, it was not highly hygroscopic, with a 3.5% weight uptake between 0 and 90% RH. The weight uptake did not lead to a change in XRPD pattern upon reanalysis under ambient conditions. Thermal analysis showed a broad endotherm between ambient and 65° C. due to solvent (water) loss (1.5% weight loss). There was a melting transition with onset at 150° C., with no change in XRPD pattern on heating up to the melt. Neither storage at 40° C. at 75% $R^H$ for 10 weeks nor handling during solubility analysis produced any significant changes. Its retention of crystallinity upon heating and its storage stability make Polymorph IV a good candidate for development in pharmaceutical formulations. Representative XRPD, DSC, and GVS data for Polymorph IV are shown in FIGS. 1d, 2c, and 3c, respectively. Representative FT-IR, FT-Raman, $^{13}C$ solid state NMR and $^{15}N$ solid state NMR data for Polymorph IV are shown in FIGS. 5, 6, 7 and 8 respectively.

Polymorph IV can be prepared from Polymorph II by maturation (repeated heating and cooling cycles) in diisopropyl ether. A $C_5$-$C_7$ alkane or alkene, such as (preferably) heptane also can used—the material so produced initially contained some Polymorph II, which, however, was removed (as determined by XRPD) after drying under vacuum. The number of cycles is at least two, preferably 3, though a larger number of cycles (e.g., up to 12) can be used. The temperature range for the cycles is typically between 5 and 50° C., preferably between 25 and 50° C. over a 24 h period.

Additionally, we also discovered several other polymorphs of Compound Ia, the preparation and characteristics of such other polymorphs being summarized below. For varying reasons, these polymorphs are less desirable than Polymorphs II and IV for formulation development.

Polymorph III is a polymorph obtained after maturation (repeated heating and cooling cycles) of the amorphous stearate salt of Compound Ia in DIPE. This polymorph could not be isolated on scale-up and was not investigated further. FIG. 1c shows representative XRPD data for Polymorph III.

Polymorph V was prepared by maturation in t-butylmethyl ether ("TBME"). It was characterized as a white powder with small particle size (<10 μm) and no definable morphology. It was crystalline by XRPD and its aqueous solubility was 0.72 mg/mL. Thermal analysis showed a melting transition with onset at 100° C. This correlated with an 8.7% weight loss by TGA, equivalent to 1 mole of TBME, suggesting that Polymorph V is a mono TBME solvate. Polymorph V decreased in crystallinity after one week's storage at 40° C. and 75% RH and converted to Polymorph II during solubility analysis. Its being a solvate militated against its desirability as a candidate for formulation development. Representative XRPD and DSC data for Polymorph V are shown in FIGS. 1e and 2d respectively.

Polymorph VI is a partially crystalline polymorph obtained from ethyl acetate, isopropyl acetate, or anisole. Small, stepped weight losses were observed during thermogravimetric analysis (TGA), suggesting that it is a family of isostructural solvates. The endotherm onset for the ethyl acetate derived form was 107° C.; the corresponding onset for the isopropyl acetate form was 90° C. The anisole form had two endotherms, with onsets at 98 and 110° C. Polymorph VI converted to Polymorph IV upon storage at 40° C. at 75% RH or to Polymorph IV or II during solubility analysis. Its conversion to Polymorph IV suggests that it is not stable enough to be a desirable candidate for formulation development. Representative XRPD, DSC, and GVS data for Polymorph VI (ethyl acetate form) are shown in FIGS. 1f, 2e, and 3d, respectively.

Polymorph VII was obtained after maturation in toluene. It was characterized as a white powder with small particle size (<20 μm) with no discernable morphology. It was partially crystalline by XRPD. Its aqueous solubility was 0.75 mg/mL. It showed constant weight loss by gravimetric vapor sorption ("GVS") analysis, with a corresponding loss of crystallinity according to XRPD re-analysis under ambient conditions. Thermal analysis showed a melting transition with an onset at 103° C. accompanied by a 4.7% weight loss by TGA, equivalent to 0.5 mole of toluene. Thus, it appears that Polymorph VII is a hemi-toluene solvate. Polymorph VII lost crystallinity after One week's storage at 40° C. and 75% RH and converted to a mixture of Polymorphs II and IV during solubility analysis. Its being a solvate and its instability made it a less desirable candidate for formulation development. Representative XRPD, DSC, and GVS data for Polymorph VII are shown in FIGS. 1g, 2f, and 3e, respectively.

FIG. 1b shows a representative XRPD pattern for Polymorph II. Table 1 is a tabulation of the major peaks in FIG. 1b. Thus, in one aspect, Polymorph II can be defined by its characteristic XRPD peaks at 3.5±0.1, 6.9±0.1, 9.2±0.1, 9.6±0.1, and 10.4±0.1 degrees 2θ or by its characteristic XRPD peaks at 3.5±0.1, 6.9±0.1, 9.2±0.1, 10.4±0.1 and 18.0±0.1 degrees 2θ.

TABLE 1

XRPD Data for Purified Polymorph II of Compound Ia

| Peak No. | Angle 2θ (degrees) | Relative Intensity (%) |
|---|---|---|
| 1 | 3.5 | 22.5 |
| 2 | 6.2 | 12.7 |
| 3 | 6.9 | 100.0 |
| 4 | 7.9 | 18.0 |
| 5 | 8.5 | 12.7 |
| 6 | 9.2 | 26.2 |
| 7 | 9.6 | 47.7 |
| 8 | 10.4 | 23.4 |
| 9 | 11.0 | 14.2 |
| 10 | 11.9 | 13.0 |
| 11 | 12.4 | 16.5 |
| 12 | 13.8 | 19.2 |
| 13 | 14.7 | 15.4 |
| 14 | 15.2 | 17.9 |
| 15 | 18.0 | 22.9 |
| 16 | 19.5 | 31.4 |
| 17 | 21.8 | 29.4 |
| 18 | 22.6 | 17.5 |

FIG. 1d shows a representative XRPD pattern for Polymorph IV. Table 2 is a tabulation of major peaks in FIG. 1d. Thus, in one aspect, Polymorph IV can be defined by its characteristic XRPD peaks at 3.8±0.1, 7.5±0.1, 8.1±0.1, 9.6±0.1, and 11.0±0.1 degrees 2θ or by its characteristic XRPD peaks at 3.8±0.1, 7.5±0.1, 16.1±0.1, 16.5±0.1, and 17.1±0.1 degrees 2θ.

TABLE 2

XRPD Data for Purified Polymorph IV of Compound Ia

| Peak No. | Angle 2θ (degrees) | Relative Intensity (%) |
|---|---|---|
| 1 | 3.8 | 52.3 |
| 2 | 6.5 | 20.7 |

TABLE 2-continued

XRPD Data for Purified Polymorph IV of Compound Ia

| Peak No. | Angle 2θ (degrees) | Relative Intensity (%) |
|---|---|---|
| 3 | 7.5 | 33.3 |
| 4 | 8.1 | 45.7 |
| 5 | 8.9 | 15.9 |
| 6 | 9.6 | 100.0 |
| 7 | 11.0 | 83.0 |
| 8 | 11.3 | 28.1 |
| 9 | 12.2 | 27.2 |
| 10 | 13.0 | 25.8 |
| 11 | 13.3 | 31.8 |
| 12 | 13.6 | 25.0 |
| 13 | 14.4 | 25.6 |
| 14 | 15.4 | 25.5 |
| 15 | 16.1 | 37.4 |
| 16 | 16.5 | 43.2 |
| 17 | 17.1 | 39.5 |
| 18 | 17.4 | 38.5 |
| 19 | 19.3 | 31.4 |
| 20 | 20.2 | 28.6 |
| 21 | 21.1 | 38.0 |
| 22 | 21.8 | 20.9 |
| 23 | 22.2 | 23.7 |

FIG. 2c shows a representative DSC scan of Polymorph IV. (In this instance, the sample of Polymorph IV was prepared with DIPE according to Example 4.) Polymorph IV exhibits a broad endotherm between ambient temperature and 110° C., attributable to solvent loss, followed by a melting endotherm with an onset at 143-156° C. and a minimum at 149-161° C. Such an endotherm is absent in the other polymorphs of Compound Ia identified by us. Thus, in one aspect, Polymorph IV can be characterized as having a melting endotherm with an onset temperature of between about 143 and about 156° C., distinguishing it from the other polymorphs of Compound Ia.

FIG. 3c shows a representative GVS scan of Polymorph IV at a constant temperature of 25° C. Polymorph IV exhibits a 3.5% mass uptake between 0 and 90% RH. The mass gain/loss is very uniform upon multiple sorption and desorption cycles. Polymorphs I (FIG. 3a), II (FIG. 3b), and VI (FIG. 3d) exhibited mass uptakes of 6-10% between 0 and 90% RH, and their mass gain/loss changed drastically upon multiple sorption and desorption cycles. Polymorph VII (FIG. 3e) exhibited a 3% mass uptake between 0 and 90% RH, but its mass gain/loss also changed drastically upon multiple sorption and desorption cycles. Thus, in one aspect, Polymorph IV can be characterized as having a 3.5% mass uptake between 0 and 90% RH (at 25° C.) and a uniform mass gain/loss upon multiple sorption and desorption cycles.

FIG. 5 shows a representative FT-IR scan of Polymorph IV. The following main absorption bands (cm$^{-1}$) may be noted (s=strong, m=medium, w=weak, experimental error is +/−2 cm$^{-1}$): 3381(m), 2973(m), 2936(m), 1721(m), 1674(m), 1558(w), 1450(m), 1408(w), 1375(m), 1347(m), 1325(w), 1272(w), 1250(w), 1176(s), 1167(s), 1130(w), 1108(s) 1080 (w), 1053(w), 1038(w), 1029(w), 993(s), 982(w), 958(m), 930(w), 898(m), 864(w), 844(w), 833(w), 804(w), 778(w), 753(w), 724(w), 701(w) and 668(w). The following peaks are particularly distinctive: 1558(w), 1347(m), 1130(w), 1108(s) and 993(s).

FIG. 6 shows a representative FT-Raman scan of Polymorph IV. The following main Raman shifts (cm$^{-1}$) may be noted (vs=very strong, s=strong, m=medium, w=weak, experimental error is +/−2 cm$^{-1}$): 2977(vs), 2940(vs), 2916 (m), 2848(s), 2719(m), 1726(w), 1662(w), 1463(s), 1412(w), 1374(w), 1356(m), 1330(w), 1282(w), 1249(w), 1208(w), 1160(m), 1130(w), 1109(w), 1058(w), 1037(w), 1000(w), 983(w), 960(w), 933(w), 900(w), 865(m), 829(w), 812(w), 773(w), 753(w), 736(w), 670(w), 615(w), 527(w), 486(w), 460(w), 433(w), 407(w), 346(w), 279(w) and 226(w). The following shifts are particularly distinctive: 1463(s), 933(w), 736(w) and 615(w).

FIG. 7 shows a representative $^{13}$C solid state NMR scan of Polymorph IV. The following chemical shifts are observed (ppm relative to an external sample of adamantine at 29.5 ppm, intensities equivalent to peak heights in brackets): 177.6 (4.68), 177.3 (3.6), 171.7 (1.18), 170.8 (2.68), 103.2 (5.08), 101.2 (5.08), 97.1 (5.09), 95.7 (6.76), 85.6 (2.27), 80.3 (2.72), 78.2 (6.35), 77.4 (5.09), 77.1 (5.42), 76.4 (11.6), 74.7 (7.69), 74.1 (9.97), 73.9 (10.11), 73.4 (4.39), 72.1 (2.62), 71.6 (6.35), 71.2 (5.61), 69.8 (1.75), 69.5 (4.22), 68.8 (5.34), 68.4 (4.79), 66.0 (5.13), 65.3 (5.72), 62.0 (2.31), 52.9 (2.59), 51.2 (5.06), 49.5 (5.74), 45.7 (12), 44.4 (5.26), 39.9 (3.58), 36.6 (3.32), 35.6 (3.82), 35.5 (3.41), 34.6 (3.29), 34.0 (2.48), 33.5 (5.01), 32.9 (2.86), 32.8 (7.31), 32.2 (5.15), 29.4 (1.69), 28.4 (6.71), 27.1 (5.53), 26.2 (3.22), 23.6 (7.16), 23.3 (1.67), 22.6 (5.05), 22.3 (10.17), 22.1 (6.25), 21.9 (4.88), 21.4 (7.3), 21.2 (6.22), 20.6 (7.42), 20.5 (8.01), 19.9 (9.82), 19.5 (2.79), 19.2 (6.23), 18.9 (7.85), 18.4 (2.93), 17.8 (5.67), 12.7 (6.44), 11.6 (4.1), 11.3 (5.13), 9.6 (6.09) and 7.7 (7.11). The following chemical shifts are particularly distinctive: 177.6, 170.8, 45.7, 28.4, 12.7 and 7.7 ppm.

FIG. 8 shows a representative $^{15}$N solid state NMR scan of Polymorph IV. The following chemical shifts are observed (ppm relative to an external sample of DL-alanine at −331.5 ppm, intensities equivalent to peak heights in brackets): −270.8 (4.29), −273.4 (12), −342.4 (8.16) and −345.1 (9.27).

The polymorphs of the invention can be used in formulations of compound Ia, in combination with the usual non-toxic, pharmaceutically acceptable carriers for tablets, pellets, capsules, suppositories, pessaries, solutions, emulsions, suspensions, and any other form suitable for use. Polymorph IV is especially preferred for handling purposes as the drug substance and for use in solid formulations.

Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

The polymorphs of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Generally, Polymorph IV is purified as a result of a preparation procedure that converts another polymorph of Compound Ia into it. In such instance, the amount of Polymorph IV in a sample is increased relative to its amount (which could be zero) in the sample prior to the preparation procedure. Additionally, other impurities may have been removed as a result of such purification. Preferably, purified Polymorph IV contains a predominant amount of Polymorph IV, to the exclusion of other Compound Ia polymorphs.

A preferred method of making purified Polymorph IV is to dissolve Compound Ia in ethyl acetate and then adding a $C_5$-$C_7$ alkane or alkene to cause crystallization of Polymorph IV. The alkane or alkene should have a low level of water, preferably below 0.005% v/v. This procedure is somewhat sensitive to the water content in the ethyl acetate solution of Compound Ia and the crystallization temperature. Water can find its way into the solution by a couple of routes. The Compound Ia used may be in the form of a polymorph having some water content (for example, Polymorph II, a dihydrate). Or, the ethyl acetate may contain trace amounts of water. Preferably, the water content in the ethyl acetate solution of compound Ia is below 3.6%, more preferably below 1.9%, and most preferably between about 1.1 and about 1.9% (volume/volume, or v/v). The water content can be kept at the desired low levels by various techniques, used individually or in combination:

(a) Using a polymorph of Compound Ia that is not a hydrate.
(b) Pre-drying the Compound Ia used, for example, at 40° C. for 17 h under a vacuum.
(c) Using high-purity, low water content ethyl acetate or pre-drying the ethyl acetate.
(d) Drying the ethyl acetate solution prior to the addition of the $C_5$-$C_7$ alkane or alkene, for example with anhydrous sodium sulfate.

Because of the sensitivity to water content in the ethyl acetate solution, it is recommended that, prior to the addition of the $C_5$-$C_7$ alkane or alkene, its water content be calculated or assayed, and, if above 3.6%, the water content be lowered before the addition of the $C_5$-$C_7$ alkane or alkene.

The crystallization temperature can range from about 20° C. to about 36° C. Generally, where the water content in the ethyl acetate solution at or below 1.9%, temperatures above 25° C. (e.g., 25 to 36° C.) are recommended for the generation of Polymorph IV.

Examples of suitable $C_5$-$C_7$ alkane and alkenes that can be used in the above procedure (or in the alternative maturation procedure) include: n-pentane, cyclopentane, 1-pentene, 2-pentene, isopentane, neopentane, n-hexane, 1-hexene, cyclohexane, n-heptane, 1-heptene, and the like. n-Heptane is preferred.

The practice of this invention can be further understood by reference to the following examples, which are provided by way of illustration and not of limitation.

EXAMPLES

Example 1

General Analytical Procedures

XRPD patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consisted of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gave an effective 2θ range of 3.2° to 29.7°. Typically the sample would be exposed to the X-ray beam for 120 seconds.

XRPD patterns were obtained by Pharmorphix Ltd. (Cambridge, United Kingdom). X-ray powder diffraction patterns for the samples were acquired on a Siemens D5000 diffractometer using CuKα radiation (40 kV, 40 mA), θ-θ goniometer, automatic divergence and receiving slits, a graphite secondary monochromator and a scintillation counter. The data were collected over an angular range of 2° to 42° 2θ in continuous scan mode using a step size of 0.02° 2θ and a step time of 1 sec. Samples were dried under vacuum at 30° C. for 24 h prior to analysis, although other drying regimens are acceptable.

XRPD samples run under ambient conditions were prepared as flat plate specimens using powder as received without grinding. Approximately 25-50 mg of the sample was gently packed into 12 mm diameter, 0.5 mm deep cavities cut into polished, zero-background (510) silicon wafers (The Gem Dugout, 1652 Princeton Drive, Pennsylvania State College, Pa. 16803, USA). All specimens were run in the stationary mode.

GVS data was also collected by Pharmorphix, Ltd. All samples were run on a Hiden IGASorp moisture sorption analyzer running CFRSorp software. Sample sizes were typically 10 mg. A moisture adsorption-desorption isotherm was performed as outlined below, with two scans giving one complete cycle. All samples were loaded and unloaded at typical ambient (room) humidity and temperature (40% RH, 25° C.). All samples were analyzed by XRPD after GVS analysis. The standard isotherm was performed at 25° C. at 10% RH intervals over a 0 to 90% RH range.

| Scan 1 Adsorption (% RH) | Scan 2 Desorption (% RH) | Adsorption (% RH) |
|---|---|---|
| 40 | 85 | 10 |
| 50 | 75 | 20 |
| 60 | 65 | 30 |
| 70 | 45 | 40 |
| 80 | 35 | |
| 90 | 25 | |
| | 15 | |
| | 5 | |
| | 0 | |

The water content of ethyl acetate, n-heptane, and compound Ia was determined by the Karl Fischer method. The water content of compound Ia/ethyl acetate solutions was calculated based on mass balance and the results were expressed as % v/v.

FT-IR data was acquired using a ThermoNicolet Avatar 360 FTIR spectrometer equipped with a Smart Golden Gate™ single reflection ATR accessory (diamond ATR crystal with zinc selenide optics) and d-TGS KBr detector. The spectrum was collected at 2 cm$^{-1}$ resolution and a co-addition of 256 scans. Happ-Genzel apodization was used. Because the FT-IR spectrum was recorded using single reflection ATR, no sample preparation was required. Using ATR FT-IR will cause the relative intensities of infrared bands to differ from those seen in an absorbance FT-IR spectrum using KBr disc or nujol mull sample preparations. Due to the nature of ATR FT-IR, the bands at lower wavenumber are more intense than those at higher wavenumber. Experimental error, unless otherwise noted, was ±2 cm$^{-1}$. Peaks were picked using ThermoNicolet Omnic 6.1a software. Intensity assignments are relative to the major band in the spectrum so they are not based on absolute values measured from the baseline. When assessing split peaks, the intensity value was taken from the baseline but again the intensity was assigned relative to the strongest band in the spectrum.

FT-Raman data was collected using a Bruker Vertex70 FT-IR spectrometer with a RamII FT-Raman module equipped with a 1064 nm NdYAG laser and LN-Germanium detector. All spectra were recorded using 2 cm$^{-1}$ resolution and Blackman-Harris 4-term apodisation, 300 mW laser power and 4096 scans. The sample was measured directly from its glass vial and exposed to the laser radiation. The data is presented as intensity as a function of Raman shift and is corrected for instrument response and frequency dependent scattering using a white light spectrum from a reference lamp using the Bruker Raman Correct function (Bruker software—OPUS 6.0). Experimental error, unless otherwise noted, was ±2 cm$^{-1}$. Peaks were picked using ThermoNicolet Omnic 6.1a software. Intensity assignments are relative to the major band in the spectrum so they are not based on absolute values measured from the baseline. When assessing split peaks, the intensity value was taken from the baseline but again the intensity was assigned relative to the strongest band in the spectrum.

Solid state $C^{13}$ and $N^{15}$ NMR data were collected at ambient conditions on a Bruker-Biospin 4 mm CPMAS probe positioned into a standard-bore Bruker-Biospin Avance 500 MHz NMR spectrometer. The nitrogen spectrum was collected using 7 mm BL CPMAS probe. The sample was packed into 4 and 7 mm $ZrO_2$ rotors, placed at the magic angle and spun at 7.0 kHz. The carbon and nitrogen spectra were collected using a proton decoupled cross-polarization magic angle spinning experiment (CPMAS). The cross-polarization time was set to 2.5 ms. The proton decoupling field of approximately 90 kHz (4 mm probe) and 70 kHz (7 mm probe) was applied. 5120 ($^{13}$C) and 30,000 ($^{15}$N) scans were collected. The recycle delays were adjusted to approximately $1.5*T_{1H}$ (where $T_{1H}$ stands for the proton longitudinal relaxation time calculated based on a proton detected proton inversion recovery relaxation experiment). The carbon spectrum was referenced using an external standard of crystalline adamantane, setting its upfield resonance to 29.5 ppm. The nitrogen spectrum was referenced using an external standard of crystalline 98% $^{15}$N labelled D,L-alanine, setting its resonance to −331.5 ppm.

Example 2

General Procedure for Preparation of Compound Ia

Compound Ia was prepared as described in the Liu '616 Application, incorporated herein by reference. FIG. 7 summarizes the synthetic scheme employed. Erythromycin A (1) was reduced with sodium borohydride to produce intermediate (9S)-dihydroerythromycin A (7). Demethylation of (9S)-dihydroerythromycin A (7) with iodine in the presence of a base such as sodium acetate or tris(hydroxymethyl)aminomethane ("TRIS") yielded N-desmethyl-(9S)-dihydroerythromycin A (8), whose alkylation with 2-iodopropane in turn yielded intermediate 9. Alkylation of intermediate 9 with N-methylbromoacetamide produced compound Ia. The polymorph of compound Ia obtained will depend on the post-chemistry isolation and purification steps.

The preparation of intermediate 9 is also described in Santi et al., U.S. Pat. No. 6,946,482 B2 (2005), incorporated herein by reference. The demethylation step is also described in Liu, U.S. application Ser. No. 11/591,726, filed Nov. 1, 2006, the disclosure of which is incorporated herein by reference.

Example 3

Preparation of Compound Ia and Isolation as Polymorph I

A 5-liter three-neck round bottom flask equipped with a mechanical stirrer and an internal thermocouple temperature probe was charged with as solution of compound 9 (156.7 g, 205 mmol), N-methyl bromoacetamide (37.4 g, 246 mmol) in dry tetrahydrofuran ("THF", 1,800 mL), with cooling to 0° C. in an ice bath. Solid potassium t-butoxide (25.3 g, 226 mmol, 1.1 eq.) was added in one batch with stirring and under nitrogen. The reaction mixture was stirred at 0° C. for 1 h. Thin layer chromatography (1:2 hexane-acetone eluent) showed that the reaction was complete. The reaction was quenched by adding saturated $NaHCO_3$ solution (300 mL). The mixture was partitioned between dilute NaHCO$_3$ (2,500 mL) and ethyl acetate ("EtOAc," 1,500 mL). The aqueous layer was extracted with EtOAc (2×1,500 mL). The combined organic layers were dried over Na$_2$SO$_4$. Crude compound Ia (178.1 g) was obtained as a slightly yellow solid, which was then purified on a silica gel column (2,800 g silica gel, 20 to 40% acetone in hexane elution gradient, 1% triethylamine) to give pure compound Ia (135 g, 79% yield).

To remove trace solvents and triethylamine, the above product was repeatedly dissolved in dichloromethane and subjected to four rotary evaporator cycles and then dried under high vacuum. It was then lyophilized from acetonitrile-water (1:1 v/v, 4 mL/g), dried in a vacuum oven (16 h, 50° C.) to give the final product (mp 106-108° C. by capillary melting point apparatus). This work-up procedure yields compound Ia as Polymorph I (note the slight endotherm as circa 110° C. in the DSC of Polymorph I in FIG. 2a.) The Liu '616 Application reported a similar melting point, so it appears that this is the polymorph described there.

Example 4

Preparation of Compound Ia and Isolation as Polymorph II

Compound 9 (light orange material, 353 g, 462 mmol) and N-bromoacetamide (84 g, 600 mmol, 1.3 eq) were dissolved in THF (3.9 L, anhydrous and inhibitor-free). The yellow solution was cooled to 0±2° C., diluted with 1 M potassium t-butoxide in THF (549 mL, 549 mmol, 1.2 eq.) over 20 min, while maintaining the temperature between 0 and 3° C. Stirring was continued at 0±2° C. while the progress of the reaction was monitored by in-process HPLC for disappearance of starting material. After 15 min, only about 0.34% of the starting material remained. The reaction was quenched with 5% NaHCO$_3$ (2.6 L). The layers were separated and the aqueous phase was extracted with EtOAc (2.9 L). The combined organic layers were washed with water (1.2 L) and then brine (1.2 L). The organic phase was dried over MgSO$_4$ (75 g). The drying agent was removed by filtration and rinsed with EtOAc (200 mL). The combined filtrates were concentrated to yield compound Ia as a light yellow residue (392 g).

The residue was dissolved in acetone (3.1 L, 8 mL/g) and the light yellow solution was diluted with deionized water (3.1 L). The slightly turbid solution was cooled to 0 to 5° C. range over 20 min, resulting in a precipitate (crystals visible at circa 10° C.). The suspension was stirred for 15 min at 0-5° C. and diluted with additional deionized water (3.1 L) over 30 min. The mixture was stirred for an additional 30 min at 0-5° C. The solids were isolated by filtration and then rinsed with a mixture of acetone (0.15 L) and deionized water (0.30 L). The solids were air-dried overnight (ca. 16 h) and then dried further (30° C.; 29 in. Hg) for 64 h to give Compound Ia (322 g) as an off-white solid.

Example 5

Preparation of Polymorph IV

DIPE (1.0 mL) was added to compound (Ia) polymorph II (250 mg) in a small screw-top vial. The vial and its contents were subjected to three heating and cooling cycles between ambient temperature and 50° C. over a 24 h period. The resulting solid was filtered and analyzed by XRPD after drying at 30° C. for 24 h, which showed that conversion to Polymorph IV had occurred.

$^1$H-NMR analysis of the Polymorph IV so obtained showed trace amounts (0.9%; 0.07 equivalents) of DIPE present. The DIPE was removed by slurrying in water as follows: water (1.0 mL) was added to a sample Polymorph IV (30 mg) in a small screw-cap vial and shaken at 25° C. for 72 h. The resulting solid was filtered and dried. Analysis by XRPD and $^1$H-NMR showed that the DIPE had been removed, without changing the form of the sample.

Example 6

Alternative Preparation of Polymorph IV

Compound Ia (2.0 g) was dissolved in ethyl acetate (12.0 mL) at ambient temperature. The water content of the ethyl acetate solution was 1.1% v/v. The light yellow solution was placed in a 500 mL three-neck round bottom flask equipped with an overhead stirrer (1 KA RW16 basic). The solution was stirred at 32° C. at 180-185 rpm and n-heptane (80 mL) was added at a rate of 0.8 mL/min using a syringe pump (KdScientific). Heptane addition was interrupted for 4 min after 50 mL of heptane had been added, to permit refilling of the syringe. After another 30 mL of heptane (for a total amount of 80 mL) had been added, the resulting suspension was stirred for another 2.5 h at 185 rpm and 32° C. The suspended crystals of Polymorph IV were collected by filtration using a ceramic 5 cm Buchner funnel and Whatman #4 filter paper. The crystals were rinsed with 90:10 v/v heptane: ethyl acetate (20 mL) and air dried for 10 min. The crystals were further dried at 40° C. under vacuum (29.5 in Hg) for 16 h, yielding 1.62 g of Polymorph IV. The identity of the product as Polymorph IV was confirmed by DSC and XRPD.

The experiment was repeated at 25° C., which also produced Polymorph IV (albeit with a slightly lower yield).

Example 7

Another Alternative Preparation of Polymorph IV

This example describes the preparation of Polymorph IV by maturation in n-heptane. n-Heptane (500 μL) was added to Polymorph I in a small screw-cap vial. The vial was subjected to 12 heat/cool cycles between 5 and 40° C. over a 24 h period, with stirring. XRPD analysis confirmed the production of Polymorph IV. The same procedure can be used with DIPE.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. Purified polymorph IV of a compound having a structure represented by formula Ia

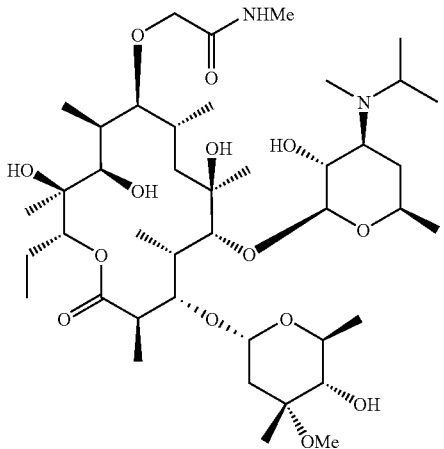

(Ia)

characterized by XRPD peaks at 3.8, 7.5, 16.1, 16.5, and 17.1 degrees 2θ (±0.1) obtained using copper K-alpha$_1$ X-rays (wavelength=1.5406 Angstroms).

2. Purified polymorph II of a compound having a structure represented by formula Ia

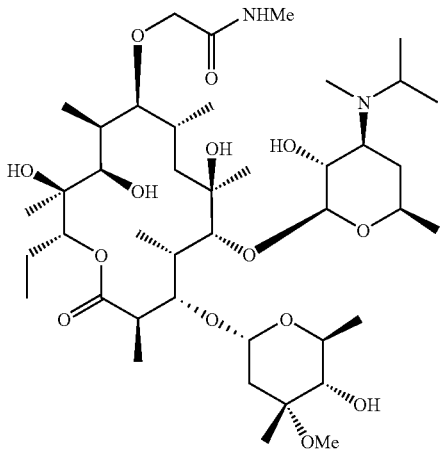

(Ia)

characterized by XRPD peaks at 3.5, 6.9, 9.2, 10.4 and 18.0 degrees 2θ (±0.1) obtained using copper K-alpha$_1$ X-rays (wavelength=1.5406 Angstroms).

3. A method for preparing a purified Polymorph IV of a compound having a structure represented by formula Ia, as defined in claim 1, comprising subjecting a polymorph of the compound, which is different from the Polymorph IV, to plural heating and cooling cycles in the presence of a medium selected from diisopropyl ether and a $C_5$-$C_7$ alkane or alkene.

4. The method according to claim 3, wherein the medium is heptane.

5. A pharmaceutical formulation comprising purified Polymorph IV of a compound having a structure represented by formula Ia, as defined in claim 1, and a pharmaceutically acceptable excipient, wherein the formulation is a solid dosage form.

6. A method of treating a disease of impaired gastric motility, comprising administering to a subject in need of such treatment a therapeutically effective amount of a purified Polymorph IV of a compound having a structure represented by formula Ia, as defined in claim 1 in a solid dosage form.

7. The method according to claim 6, wherein the disease of impaired gastric motility is gastroesophageal reflux disease ("GERD").

8. A pharmaceutical formulation comprising purified Polymorph II of a compound having a structure represented by formula Ia of claim 2, and a pharmaceutically acceptable excipient, wherein the formulation is a solid dosage form.

9. A method of treating a disease of impaired gastric motility, comprising administering to a subject in need of such treatment a therapeutically effective amount of a purified Polymorph II of a compound having a structure represented by formula Ia of claim 2 in a solid dosage form.

10. The method according to claim 9, wherein the disease of impaired gastric motility is gastroesophageal reflux disease ("GERD").

* * * * *

UNITED STATES PATENT AND TRADEMARK OFFICE
CERTIFICATE OF CORRECTION

PATENT NO. : 8,030,282 B2
APPLICATION NO. : 12/762190
DATED : October 4, 2011
INVENTOR(S) : Licari et al.

It is certified that error appears in the above-identified patent and that said Letters Patent is hereby corrected as shown below:

On the Title page, Item [56] col. 2, line 4,

Delete "-4-" and insert -- -4"- --, therefor;

On the Title page, Item [56] col. 2, line 8,

Delete "-4-" and insert -- -4"- --, therefor; and

On the Title page, Item [56] col. 2, line 14,

Delete "-4-" and insert -- -4"- --, therefor.

Signed and Sealed this
Twentieth Day of August, 2013

Teresa Stanek Rea
*Acting Director of the United States Patent and Trademark Office*